US010335154B2

(12) United States Patent
Johnson et al.

(10) Patent No.: US 10,335,154 B2
(45) Date of Patent: Jul. 2, 2019

(54) POLYMERIC ELECTROSPUN EMBOLIZATION DEVICE AND METHODS OF USE

(71) Applicant: IkoNano Venture Partners, LLC, Columbus, OH (US)

(72) Inventors: Jed Johnson, London, OH (US); Tyler Groehl, Columbus, OH (US); Devan Ohst, Columbus, OH (US)

(73) Assignee: IkoNano Venture Partners, LLC, Columbus, OH (US)

( * ) Notice: Subject to any disclaimer, the term of this patent is extended or adjusted under 35 U.S.C. 154(b) by 129 days.

(21) Appl. No.: 15/263,320

(22) Filed: Sep. 12, 2016

(65) Prior Publication Data

US 2017/0071607 A1    Mar. 16, 2017

Related U.S. Application Data

(60) Provisional application No. 62/216,553, filed on Sep. 10, 2015, provisional application No. 62/324,629, filed on Apr. 19, 2016.

(51) Int. Cl.
*A61B 17/12* (2006.01)
*A61B 17/00* (2006.01)
(Continued)

(52) U.S. Cl.
CPC .... *A61B 17/12113* (2013.01); *A61B 17/1214* (2013.01); *A61B 2017/00526* (2013.01);
(Continued)

(58) Field of Classification Search
CPC ...................... A61B 17/12113; A61B 17/1214
See application file for complete search history.

(56) References Cited

U.S. PATENT DOCUMENTS 6,136,015 A * 10/2000 Kurz ................ A61B 17/12022
606/191
6,280,457 B1    8/2001 Wallace et al.
(Continued)

FOREIGN PATENT DOCUMENTS

| WO | WO 2009/086208 A2 | 7/2009 |
| WO | WO 2015/100238 A1 | 7/2015 |
| WO | 2017044982 A1 | 3/2017 |

OTHER PUBLICATIONS

International Search Report and Written Opinion for PCT/US2016/051393 dated Nov. 10, 2016.
(Continued)

*Primary Examiner* — Richard G Louis
(74) *Attorney, Agent, or Firm* — Kilpatrick Townsend and Stockton LLP

(57) ABSTRACT

An embolization device may include a fiber section having a plurality of polymeric electrospun fibers and, optionally, a contrast agent. An embolization device may further include a plurality of fiber sections, wherein each fiber section is separated by a linker. A method of deploying such an embolization device may include inserting the embolization device into a vessel. The method may further include applying an electrical current to one or more of the linkers, applying electrothermal heat to at least a portion of the device, or applying force to at least a portion of a delivery vehicle for the device. A method of manufacturing the device may include electrospinning a fiber section, and processing the fiber section by straining, twisting, heating, or shaping it.

34 Claims, 39 Drawing Sheets

(51) Int. Cl.
*D01D 5/00* (2006.01)
*A61B 90/00* (2016.01)

(52) U.S. Cl.
CPC ............ *A61B 2017/00898* (2013.01); *A61B 2017/00942* (2013.01); *A61B 2017/12063* (2013.01); *A61B 2017/12068* (2013.01); *A61B 2090/3966* (2016.02); *D01D 5/0007* (2013.01)

(56) References Cited

U.S. PATENT DOCUMENTS

| | | | |
|---|---|---|---|
| 6,312,421 | B1 | 11/2001 | Boock |
| 6,620,152 | B2 | 9/2003 | Guglielmi |
| 6,635,082 | B1 | 10/2003 | Hossainy et al. |
| 7,323,000 | B2 | 1/2008 | Monstdt et al. |
| 8,182,506 | B2 | 5/2012 | Fitz et al. |
| 8,273,116 | B2 | 9/2012 | Licata et al. |
| 2002/0128680 | A1* | 9/2002 | Pavlovic ............... A61F 2/01 606/200 |
| 2004/0098023 | A1 | 5/2004 | Lee et al. |
| 2005/0149173 | A1* | 7/2005 | Hunter ............... A61B 17/11 623/1.42 |
| 2005/0177103 | A1 | 8/2005 | Hunter et al. |
| 2006/0229668 | A1* | 10/2006 | Prestezog ....... A61B 17/12022 606/213 |
| 2007/0142859 | A1* | 6/2007 | Buiser ............ A61B 17/12022 606/200 |
| 2007/0207179 | A1 | 9/2007 | Andersen et al. |
| 2007/0232994 | A1* | 10/2007 | Sonoda ................ A61M 5/46 604/68 |
| 2007/0255422 | A1* | 11/2007 | Wei ..................... A61F 2/28 623/23.51 |
| 2009/0018643 | A1 | 1/2009 | Hashi et al. |
| 2009/0299448 | A1 | 12/2009 | Timko et al. |
| 2010/0023047 | A1* | 1/2010 | Simpson ............... A61F 2/958 606/192 |
| 2010/0070020 | A1* | 3/2010 | Hashi .................... A61L 31/06 623/1.15 |
| 2011/0046657 | A1* | 2/2011 | Guo ................ A61B 17/12022 606/200 |
| 2012/0226344 | A1* | 9/2012 | Shirokaze ........... D02G 1/0206 623/1.13 |
| 2013/0018454 | A1* | 1/2013 | Lelkes .................... A61F 2/06 623/1.32 |
| 2013/0310914 | A1 | 11/2013 | Ehrenreich et al. |
| 2014/0081414 | A1 | 3/2014 | Hall et al. |
| 2014/0141152 | A1 | 5/2014 | Sostek et al. |
| 2016/0302911 | A1* | 10/2016 | Soletti .................... A61L 27/18 |

OTHER PUBLICATIONS

Cloft and Kallmes et al., "Aneurysm Packing with HydroCoil Embolic System versus Platinum Coils: Initial Clinical Experience", AJNR Am J Neuroradiol, American Society of Neuroradiology (Jan. 2004), (25) pp. 60-62.

Henkes et al., "A system for the Endovascular Electrolytical Detachment of Platinum Coils at Variable Length", Technical Note on VDS, Interventional Neuroradiology (2002), (8) pp. 197-200.

Thammaroj et al., "Preliminary Clinical Experience in Cerebral Aneurysms in Glasgow", MTI (Dendron) Variable Detachable Coils, Interventional Neuroradiology (2003), (9) pp. 47-52.

Watanabe et al., "Packing efficacy of hydrocoil embolic system: in vitro study using ruptured aneurysm model", Neurosurgical Review (Apr. 2007), 30(2) pp. 127-130.

\* cited by examiner

810

POLYMERIC ELECTROSPUN EMBOLIZATION DEVICE AND METHODS OF USE

CROSS-REFERENCE TO RELATED APPLICATIONS

This application claims priority to and benefit of U.S. Provisional Application Ser. No. 62/216,553, filed Sep. 10, 2015, entitled "Polymeric Electrospun Embolization Device and Methods of Use," and U.S. Provisional Application Ser. No. 62/324,629, filed Apr. 19, 2016, entitled "Polymeric Electrospun Embolization Device and Methods of Use," each of which is hereby incorporated herein by reference in its entirety.

BACKGROUND

Pathologies such as aneurysms, parent vessel occlusions, carotid venous fistulas, and arteriovenous malformations may be treated with an embolization device. An aneurysm, for example, is a localized, balloon-like bulge in the wall of a blood vessel. Aneurysms occur due to a weakened blood vessel wall, and may result from a number of conditions, including a hereditary condition or an acquired disease. Aneurysms may occur in any blood vessel, including in vessels of the brain, heart, thoracic cavity, and abdominal cavity. As an aneurysm increases in size, its risk of rupture also increases. A ruptured aneurysm may lead to a stroke as well as rapid blood loss, which may result in death. More than 6 million people in the United States alone are living with a brain aneurysm. Each year, approximately 30,000 patients in the United States are diagnosed with a ruptured brain aneurysm requiring treatment; without treatment, about 40% of these patients will not survive.

The process of coiling may be used to treat aneurysms. The primary goal of coiling is to prevent rupture in unruptured aneurysms, and to prevent rebleeding in ruptured aneurysms. Coiling functions by packing tiny loops of a material into an aneurysm, effectively isolating the aneurysm from the native blood flow, and promoting thrombosis to close off the aneurysm. Typically, the loops of material are inserted using a catheter, and the insertion is monitored by image guidance, such as fluoroscopic image guidance. A standard coiling procedure is only effective in about one-third of patients who receive it.

A coiling procedure carries the risk of rupturing the very aneurysm it is meant to treat. Due to the stiffness of some common coil materials, such as platinum, the coils may puncture the weakened walls of the aneurysm during insertion, resulting in aneurysm rupture. The stiffness of some coil materials may also prevent the coils from reaching a high packing density, resulting in a semi-packed aneurysm. To remedy this packing issue, some platinum coil devices have employed an expanding hydrophilic coating and a series of arms to further occupy otherwise unfilled voids within the aneurysm. However, this increased packing may result in increased coil insertion difficulty, or even the inability to retract or reposition the coils in the aneurysm. Further, with conventional coiling systems, the user either must make an educated guess as to the length of coil required for a particular procedure, or use multiple coils to fill the aneurysm, which may require multiple loading and deployment processes in a time-sensitive procedure.

Therefore, there exists a need for an embolization device that may be highly flexible to allow it to conform safely to the shape of an aneurysm or vessel, resulting in a reduced risk of aneurysm rupture from the deployment of the device. Such an embolization device may also include a radiological contrast agent to allow for noninvasive monitoring of the device during and following its deployment. Optionally, the device may also include a hydrophilic component, which may allow the device to volumetrically expand beyond its original dimensions to allow for greater packing densities than a device without a hydrophilic component. Further, there exists a need for an embolization device that allows the user to choose a custom device length during the deployment of the device.

SUMMARY

In an embodiment, an embolization device may include a fiber section having a plurality of polymeric electrospun fibers and, optionally, a contrast agent. In some embodiments, an embolization device may further include a plurality of fiber sections, wherein each fiber section is separated by a linker.

In an embodiment, a method of deploying such an embolization device may include inserting the device into a blood vessel. The method may further include, for example, applying an electrical current to one or more of the linkers, applying electrothermal heat to at least a portion of the device, or applying force to at least a portion of a delivery vehicle for the device.

In an embodiment, a method of manufacturing such an embolization device may include electrospinning a fiber section, and processing the fiber section by straining, twisting, heating, or shaping it, for example.

Figure 17A:
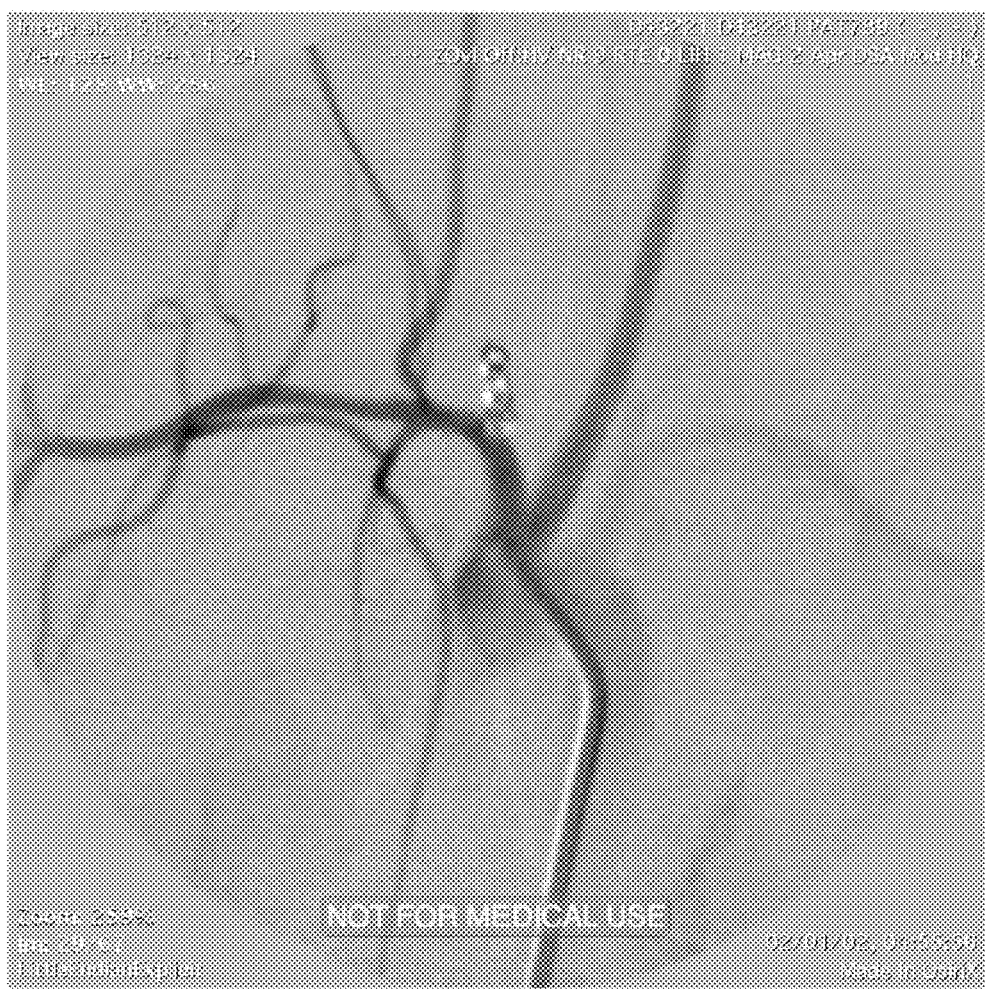
FIG. 17A illustrates an angiogram of an aneurysm in a rabbit model at day 0.
Figure 17B:
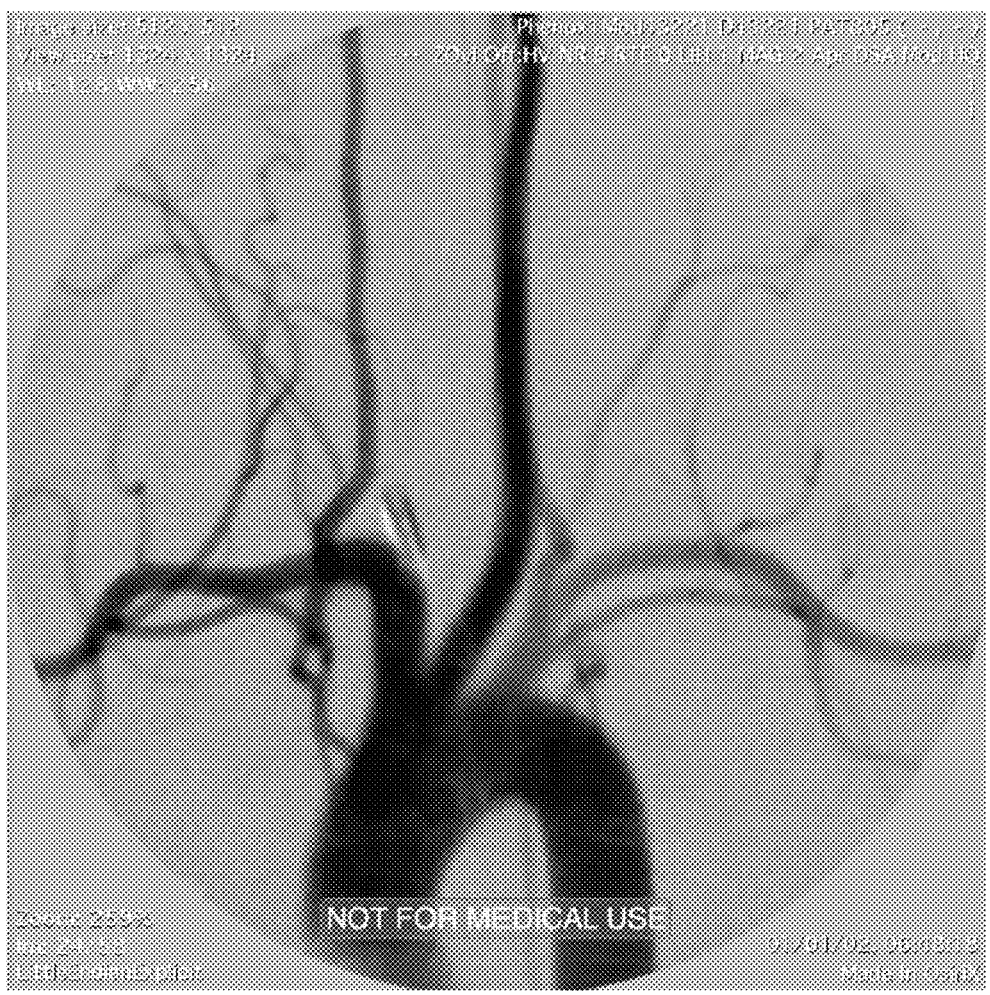
FIG. 17B illustrates an angiogram of the same aneurysm shown in FIG. 17A, 30 days after embolization with a device and method according to the present disclosure.

17F illustrates a 40× magnification of the neck of the fully embolized vessel of FIG. 17B.

Figure 18A:
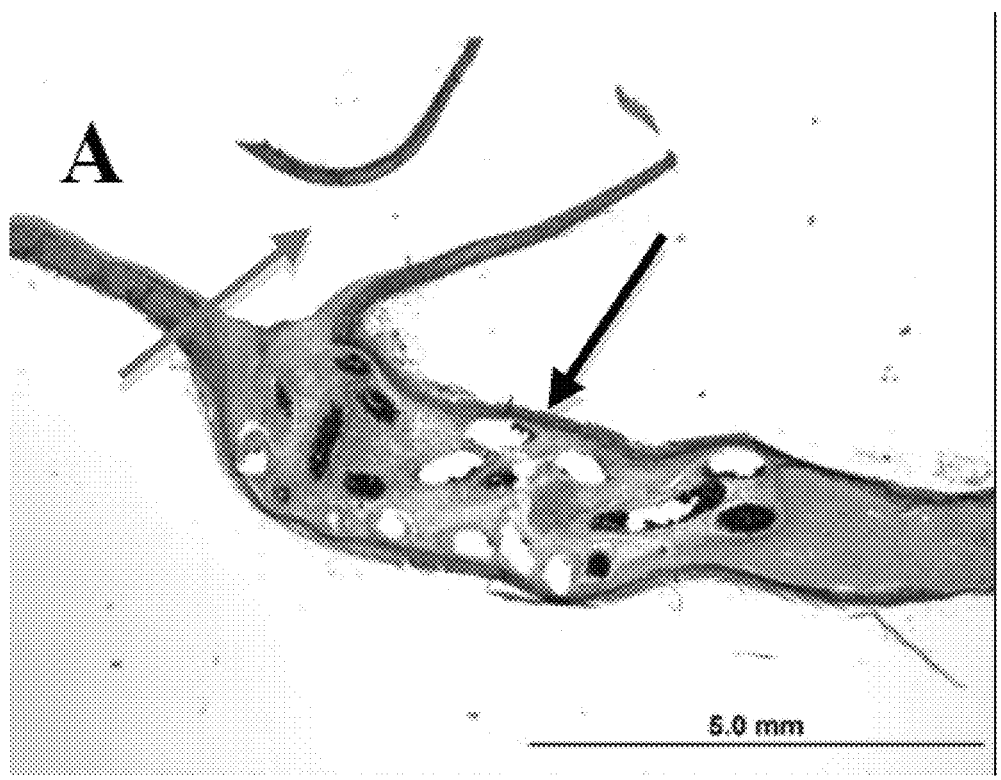

FIG. 18A illustrates histology of a whole mount coronal section through the sac (downward-facing arrow) and parent vessel (upward-facing arrow) of the vessel of FIG. 17B, using MP stain.

Figure 18B:
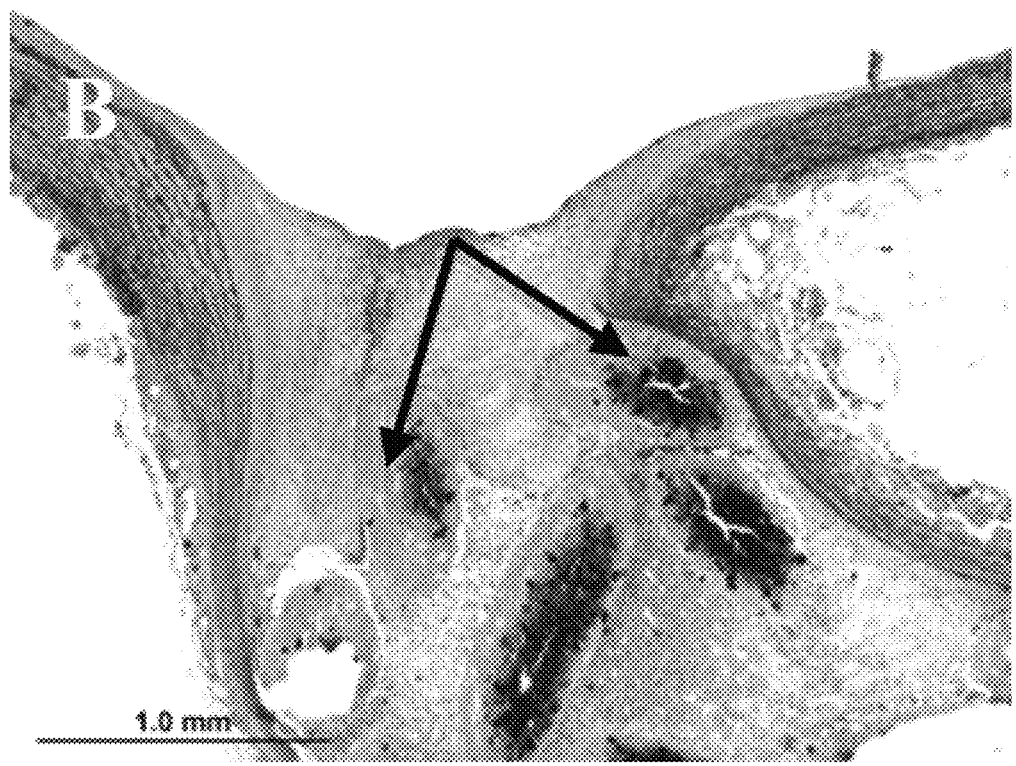

FIG. 18B illustrates histology of the aneurysm neck of the vessel of FIG. 17B covered with neointimal growth and cross sections of the embolization device in accordance with the present disclosure underneath (arrows), using MP stain.

Figure 18C:
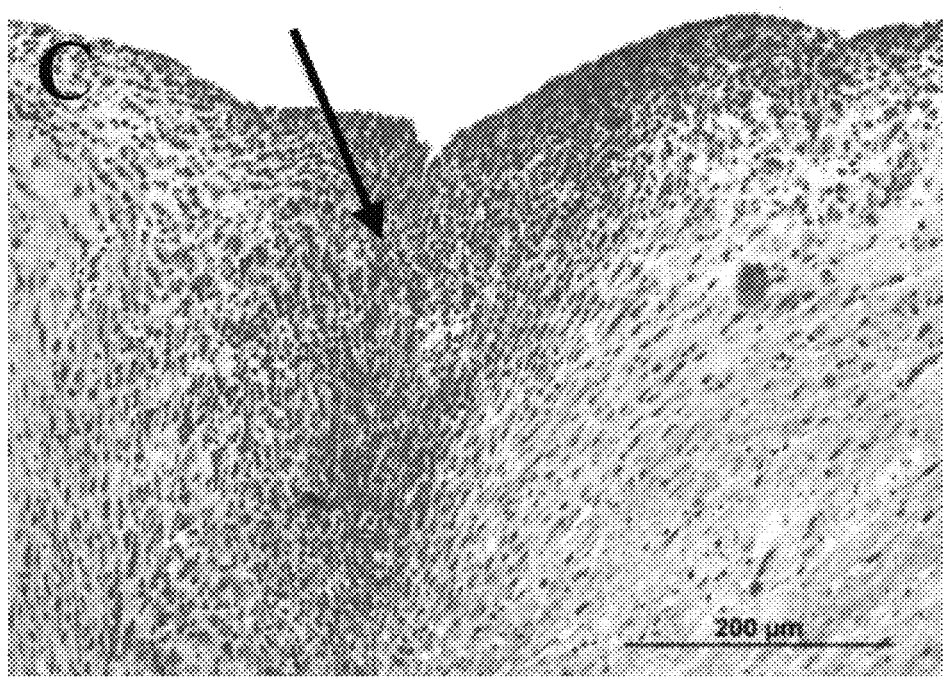

FIG. 18C illustrates histology of a close-up view of the neck of the vessel of FIG. 17B with focally marked chronic inflammatory cell infiltration (arrow), using H&E stain.

Figure 18D:
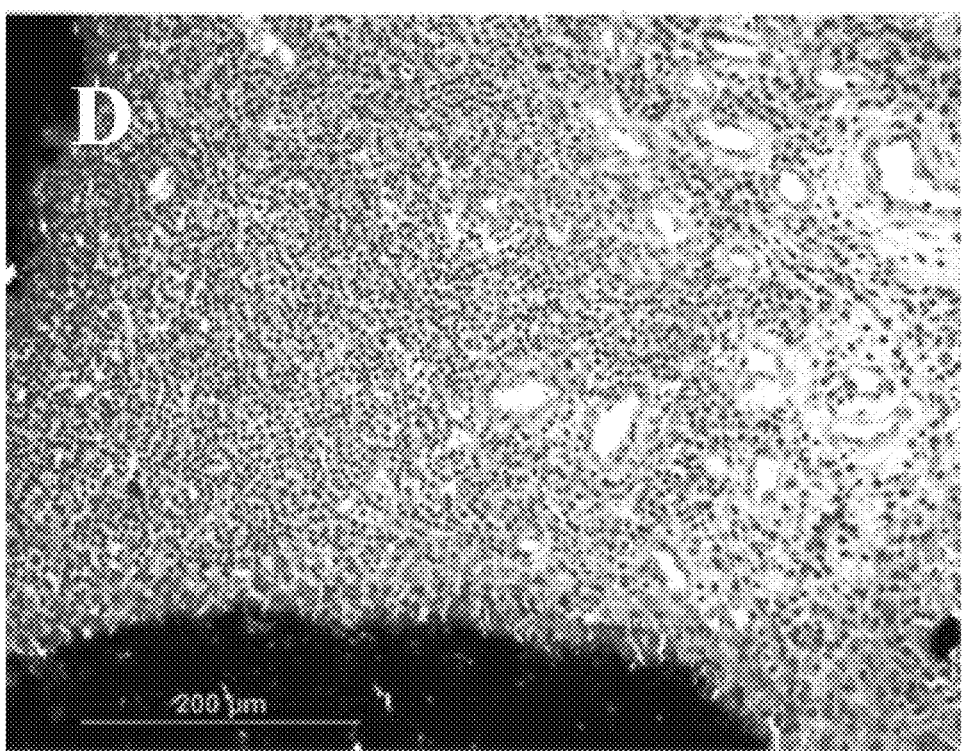

FIG. 18D illustrates histology of a large area of saccular matrix lymphocyte infiltration of the vessel of FIG. 17B, using H&E stain.

Figure 18E:
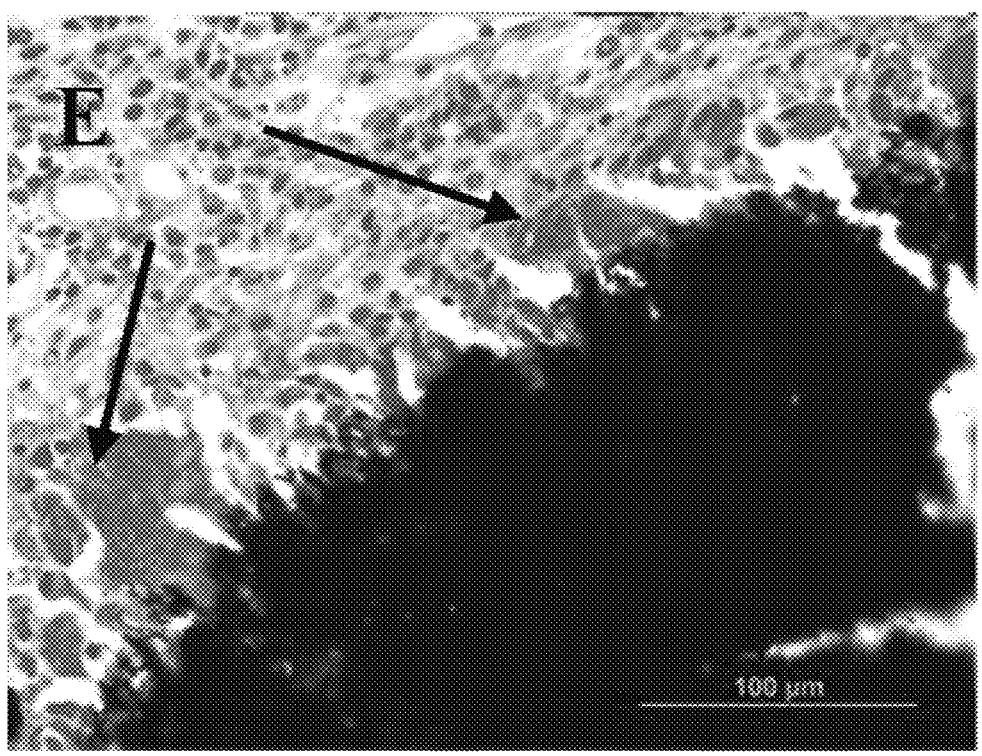

FIG. 18E illustrates histology of the macrophage and giant cell reaction of the vessel of FIG. 17B to the surface of the embolization device in accordance with the present disclosure (arrows), using H&E stain.

DETAILED DESCRIPTION

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "fiber" is a reference to one or more fibers and equivalents thereof known to those skilled in the art, and so forth.

As used herein, the term "about" means plus or minus 10% of the numerical value of the number with which it is being used. Therefore, about 50% means in the range of 40% to 60%.

Electrospinning Fibers

Electrospinning is a method which may be used to process a polymer solution into a fiber. In embodiments wherein the diameter of the resulting fiber is on the nanometer scale, the fiber may be referred to as a nanofiber. Fibers may be formed into a variety of shapes by using a range of receiving surfaces, such as mandrels or collectors. In some embodiments, a flat shape, such as a sheet or sheet-like fiber mold or fiber scaffold, may be formed by using a substantially round or cylindrical mandrel, and cutting and unrolling the resulting fiber mold to form the sheet. The resulting fiber molds or shapes may be used in many applications, including the repair or replacement of biological structures. In some embodiments, the resulting fiber scaffold may be implanted into a biological organism or a portion thereof.

Electrospinning methods may involve spinning a fiber from a polymer solution by applying a high DC voltage potential between a polymer injection system and a mandrel. In some embodiments, one or more charges may be applied to one or more components of an electrospinning system. In some embodiments, a charge may be applied to the mandrel, the polymer injection system, or combinations or portions thereof. Without wishing to be bound by theory, as the polymer solution is ejected from the polymer injection system, it is thought to be destabilized due to its exposure to a charge. The destabilized solution may then be attracted to a charged mandrel. As the destabilized solution moves from the polymer injection system to the mandrel, its solvents may evaporate and the polymer may stretch, leaving a long, thin fiber that is deposited onto the mandrel. The polymer solution may form a Taylor cone as it is ejected from the polymer injection system and exposed to a charge.

Polymer Injection System

A polymer injection system may include any system configured to eject some amount of a polymer solution into an atmosphere to permit the flow of the polymer solution from the injection system to the mandrel. In some embodiments, the polymer injection system may deliver a continuous or linear stream with a controlled volumetric flow rate of a polymer solution to be formed into a fiber. In some embodiments, the polymer injection system may deliver a variable stream of a polymer solution to be formed into a fiber. In some embodiments, the polymer injection system may be configured to deliver intermittent streams of a polymer solution to be formed into multiple fibers. In some embodiments, the polymer injection system may include a syringe under manual or automated control. In some embodiments, the polymer injection system may include multiple syringes and multiple needles or needle-like components under individual or combined manual or automated control. In some embodiments, a multi-syringe polymer injection system may include multiple syringes and multiple needles or needle-like components, with each syringe containing the same polymer solution. In some embodiments, a multi-syringe polymer injection system may include multiple syringes and multiple needles or needle-like components, with each syringe containing a different polymer solution. In some embodiments, a charge may be applied to the polymer injection system, or to a portion thereof. In some embodiments, a charge may be applied to a needle or needle-like component of the polymer injection system.

In some embodiments, the polymer solution may be ejected from the polymer injection system at a flow rate of less than or equal to about 5 mL/h per needle. In other embodiments, the polymer solution may be ejected from the polymer injection system at a flow rate per needle in a range from about 0.01 mL/h to about 50 mL/h. The flow rate at which the polymer solution is ejected from the polymer injection system per needle may be, in some non-limiting examples, about 0.01 mL/h, about 0.05 mL/h, about 0.1 mL/h, about 0.5 mL/h, about 1 mL/h, 2 mL/h, about 3 mL/h, about 4 mL/h, about 5 mL/h, about 6 mL/h, about 7 mL/h, about 8 mL/h, about 9 mL/h, about 10 mL/h, about 11 mL/h, about 12 mL/h, about 13 mL/h, about 14 mL/h, about 15 mL/h, about 16 mL/h, about 17 mL/h, about 18 mL/h, about 19 mL/h, about 20 mL/h, about 21 mL/h, about 22 mL/h, about 23 mL/h, about 24 mL/h, about 25 mL/h, about 26 mL/h, about 27 mL/h, about 28 mL/h, about 29 mL/h, about 30 mL/h, about 31 mL/h, about 32 mL/h, about 33 mL/h, about 34 mL/h, about 35 mL/h, about 36 mL/h, about 37 mL/h, about 38 mL/h, about 39 mL/h, about 40 mL/h, about 41 mL/h, about 42 mL/h, about 43 mL/h, about 44 mL/h, about 45 mL/h, about 46 mL/h, about 47 mL/h, about 48 mL/h, about 49 mL/h, about 50 mL/h, or any range between any two of these values, including endpoints.

As the polymer solution travels from the polymer injection system toward the mandrel, the diameter of the resulting fibers may be in the range of about 0.1 µm to about 10 µm. Some non-limiting examples of electrospun fiber diameters may include about 0.1 µm, about 0.2 µm, about 0.5 µm, about 1 µm, about 2 µm, about 5 µm, about 10 µm, about 20 µm, or ranges between any two of these values, including endpoints.

Polymer Solution

In some embodiments, the polymer injection system may be filled with a polymer solution. In some embodiments, the polymer solution may comprise one or more polymers. In some embodiments, the polymer solution may be a fluid formed into a polymer liquid by the application of heat. A polymer solution may include, for example, non-resorbable polymers, resorbable polymers, natural polymers, or a combination thereof.

The non-resorbable polymers may include, in some non-limiting examples, polyethylene, polyethylene oxide, polyethylene terephthalate, polyester, polymethylmethacrylate, polyacrylonitrile, silicone, polyurethane, polycarbonate, polyether ketone ketone, polyether ether ketone, polyether imide, polyamide, polystyrene, polyether sulfone, polysulfone, polyvinyl acetate, polytetrafluoroethylene, polyvinylidene fluoride, or combinations thereof.

The resorbable polymers may include, in some non-limiting examples, polycaprolactone, polylactic acid, polyglycolic acid, polydioxanone, Poly(3-hydroxybutyrate-co-3-hydroxyvalerate), trimethylene carbonate, polydiols, polyesters, or combinations thereof.

The natural polymers may include, in some non-limiting examples, collagen, gelatin, fibrin, fibronectin, albumin, hyaluronic acid, elastin, chitosan, alginate, or combinations thereof.

It may be understood that polymer solutions may also include a combination of synthetic polymers and naturally occurring polymers in any combination or compositional ratio. In some non-limiting examples, the polymer solution may comprise a weight percent ratio of, for example, polyethylene terephthalate to polyurethane, from about 10% to about 90%. Non-limiting examples of such weight percent ratios may include about 10%, about 15%, about 20%, about 25%, about 30%, about 33%, about 35%, about 40%, about 45%, about 50%, about 55%, about 60%, about 66%, about 70%, about 75%, about 80%, about 85%, about 90%, or ranges between any two of these values, including endpoints.

In some embodiments, the polymer solution may comprise one or more solvents. In some embodiments, the solvent may comprise, for example, acetone, dimethylformamide, dimethylsulfoxide, N-methylpyrrolidone, N,N-dimethylformamide, Nacetonitrile, hexanes, ether, dioxane, ethyl acetate, pyridine, toluene, xylene, tetrahydrofuran, trifluoroacetic acid, hexafluoroisopropanol, acetic acid, dimethylacetamide, chloroform, dichloromethane, water, alcohols, ionic compounds, or combinations thereof. The concentration range of polymer or polymers in solvent or solvents may be, without limitation, from about 1 wt % to about 50 wt %. Some non-limiting examples of polymer concentration in solution may include about 1 wt %, 3 wt %, 5 wt %, about 10 wt %, about 15 wt %, about 20 wt %, about 25 wt %, about 30 wt %, about 35 wt %, about 40 wt %, about 45 wt %, about 50 wt %, or ranges between any two of these values, including endpoints.

In an embodiment, the polymer solution may comprise a 2:8 blend of polyethylene terephthalate and polyurethane in hexafluoroisopropanol, with about 1000 wt % tantalum nanopowder.

In some embodiments, the polymer solution may also include additional materials. Non-limiting examples of such additional materials may include radiation opaque materials, contrast agents, electrically conductive materials, fluorescent materials, luminescent materials, antibiotics, growth factors, vitamins, cytokines, steroids, anti-inflammatory drugs, small molecules, sugars, salts, peptides, proteins, cell factors, DNA, RNA, other materials to aid in non-invasive imaging, or any combination thereof. In some embodiments, the radiation opaque materials may include, for example, barium, tantalum, tungsten, iodine, gadolinium, gold, platinum, bismuth, or bismuth (III) oxide. In some embodiments, the electrically conductive materials may include, for example, gold, silver, iron, or polyaniline.

In some embodiments, the additional materials may be present in the polymer solution in an amount from about 1 wt % to about 1500 wt % of the polymer mass. In some non-limiting examples, the additional materials may be present in the polymer solution in an amount of about 1 wt %, about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 100 wt %, about 125 wt %, about 150 wt %, about 175 wt %, about 200 wt %, about 225 wt %, about 250 wt %, about 275 wt %, about 300 wt %, about 325 wt %, about 350 wt %, about 375 wt %, about 400 wt %, about 425 wt %, about 450 wt %, about 475 wt %, about 500 wt %, about 525 wt %, about 550 wt %, about 575 wt %, about 600 wt %, about 625 wt %, about 650 wt %, about 675 wt %, about 700 wt %, about 725 wt %, about 750 wt %, about 775 wt %, about 800 wt %, about 825 wt %, about 850 wt %, about 875 wt %, about 900 wt %, about 925 wt %, about 950 wt %, about 975 wt %, about 1000 wt %, about 1025 wt %, about 1050 wt %, about 1075 wt %, about 1100 wt %, about 1125 wt %, about 1150 wt %, about 1175 wt %, about 1200 wt %, about 1225 wt %, about 1250 wt %, about 1275 wt %, about 1300 wt %, about 1325 wt %, about 1350 wt %, about 1375 wt %, about 1400 wt %, about 1425 wt %, about 1450 wt %, about 1475 wt %, about 1500 wt %, or any range between any of these two values, including endpoints.

Figure 1:
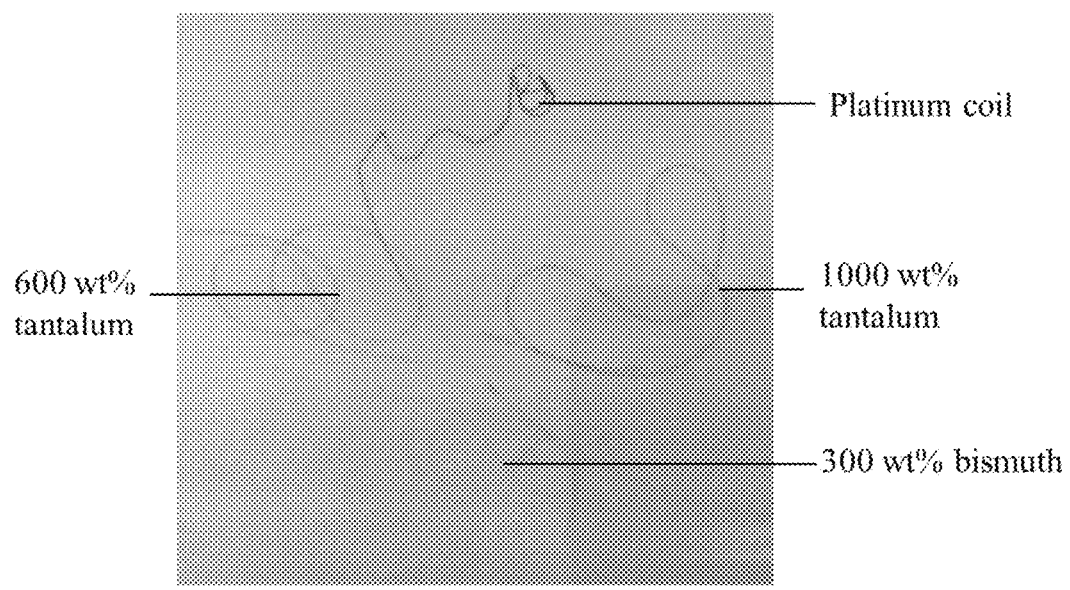
FIG. 1 illustrates a side-by-side comparison under fluoroscopy of embolization devices comprising polymeric electrospun fibers having 300 wt % bismuth, 600 wt % tantalum, and 1,000 wt % tantalum, made in accordance with the present disclosure, compared to a standard platinum coil.

FIG. 1 illustrates, for example, a side-by-side comparison under fluoroscopy of embolization devices comprising electrospun fibers having 300 wt % bismuth, 600 wt % tantalum, and 1,000 wt % tantalum, each made in accordance with the present disclosure, compared to a standard platinum coil.

The type of polymer in the polymer solution may determine the characteristics of the electrospun fiber. Some fibers may be composed of polymers that are bio-stable and not absorbable or biodegradable when implanted. Such fibers may remain generally chemically unchanged for the length of time in which they remain implanted. Alternatively, fibers may be composed of polymers that may be absorbed or bio-degraded over time. Such fibers may act as an initial template or scaffold for the repair or replacement of organs and/or tissues. These organ or tissue templates or scaffolds may degrade in vivo once the tissues or organs have been replaced or repaired by natural structures and cells. It may be further understood that a polymer solution and its resulting electrospun fiber(s) may be composed of more than one type of polymer, and that each polymer therein may have a specific characteristic, such as bio-stability or biodegradability.

Applying Charges to Electrospinning Components

In an electrospinning system, one or more charges may be applied to one or more components, or portions of components, such as, for example, a mandrel or a polymer injection system, or portions thereof. In some embodiments, a positive charge may be applied to the polymer injection system, or portions thereof. In some embodiments, a negative charge may be applied to the polymer injection system, or portions thereof. In some embodiments, the polymer injection system, or portions thereof, may be grounded. In some embodiments, a positive charge may be applied to mandrel, or portions thereof. In some embodiments, a negative charge may be applied to the mandrel, or portions thereof. In some embodiments, the mandrel, or portions thereof, may be grounded. In some embodiments, one or more components or portions thereof may receive the same charge. In some embodiments, one or more components, or portions thereof, may receive one or more different charges.

The charge applied to any component of the electrospinning system, or portions thereof, may be from about −15 kV to about 30 kV, including endpoints. In some non-limiting examples, the charge applied to any component of the electrospinning system, or portions thereof, may be about −15 kV, about −10 kV, about −5 kV, about −3 kV, about −1 kV, about −0.01 kV, about 0.01 kV, about 1 kV, about 5 kV, about 10 kV, about 12 kV, about 15 kV, about 20 kV, about 25 kV, about 30 kV, or any range between any two of these values, including endpoints. In some embodiments, any component of the electrospinning system, or portions thereof, may be grounded.

Mandrel Movement During Electrospinning

During electrospinning, in some embodiments, the mandrel may move with respect to the polymer injection system. In some embodiments, the polymer injection system may move with respect to the mandrel. The movement of one electrospinning component with respect to another electrospinning component may be, for example, substantially rotational, substantially translational, or any combination thereof. In some embodiments, one or more components of the electrospinning system may move under manual control. In some embodiments, one or more components of the electrospinning system may move under automated control. In some embodiments, the mandrel may be in contact with or mounted upon a support structure that may be moved using one or more motors or motion control systems. The pattern of the electrospun fiber deposited on the mandrel may depend upon the one or more motions of the mandrel with respect to the polymer injection system. In some embodiments, the mandrel surface may be configured to rotate about its long axis. In one non-limiting example, a mandrel having a rotation rate about its long axis that is faster than a translation rate along a linear axis, may result in a nearly helical deposition of an electrospun fiber, forming windings about the mandrel. In another example, a mandrel having a translation rate along a linear axis that is faster than a rotation rate about a rotational axis, may result in a roughly linear deposition of an electrospun fiber along a liner extent of the mandrel.

Embolization Device

Figure 2:
FIG. 2 illustrates an embodiment of polymeric electrospun fibers in accordance with the present disclosure.
Figure 3A:
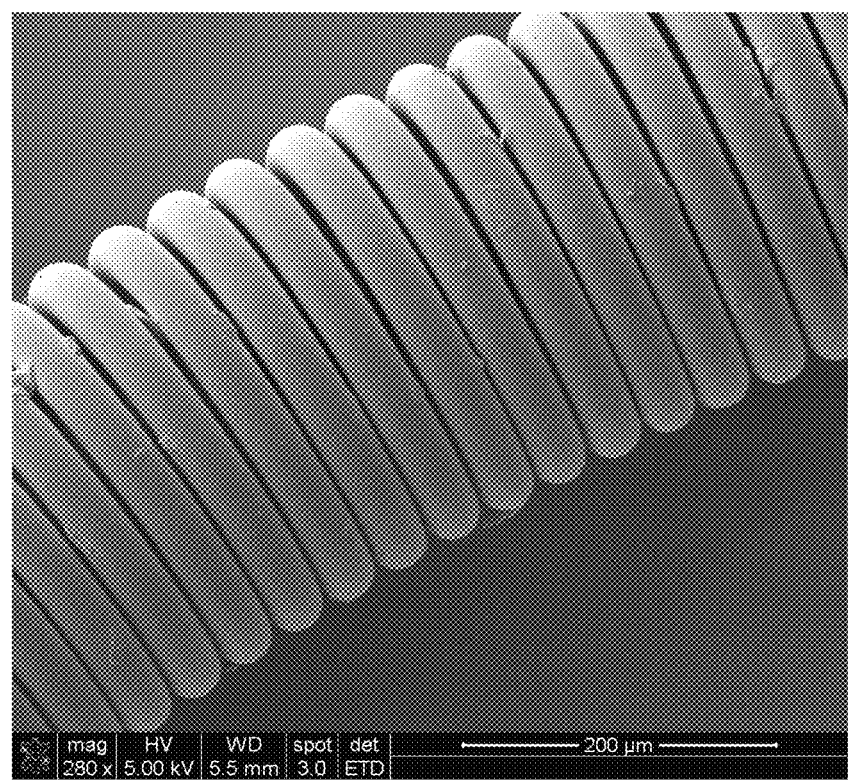
FIG. 3A illustrates scanning electron microscopy of a section of a standard platinum coil.
Figure 3B:
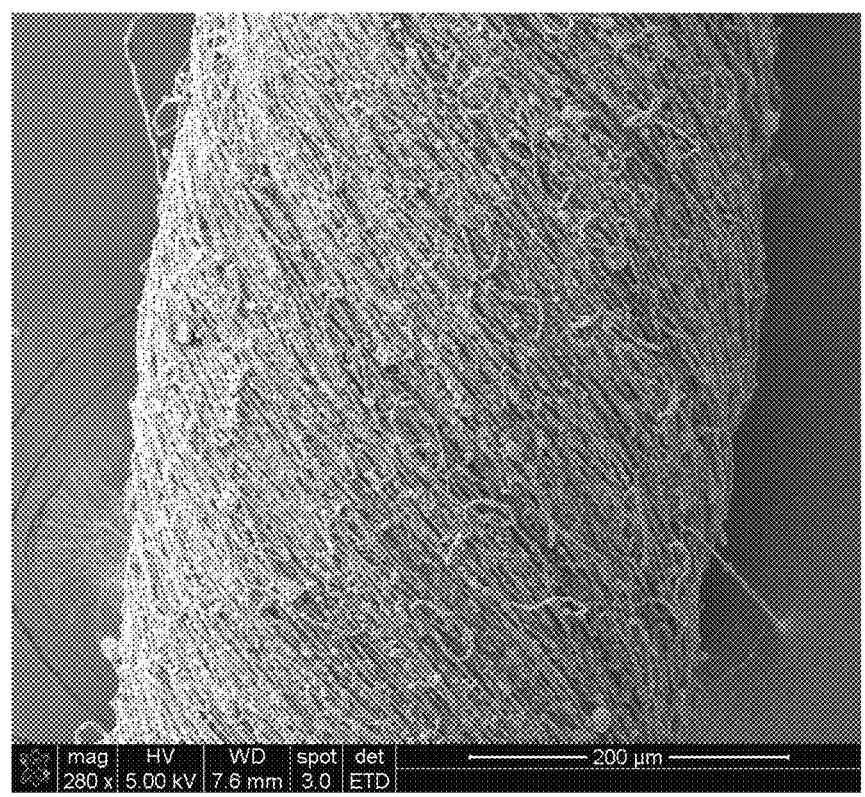
FIG. 3B illustrates scanning electron microscopy of an embodiment of a twisted fiber section in accordance with the present disclosure.
Figure 5:
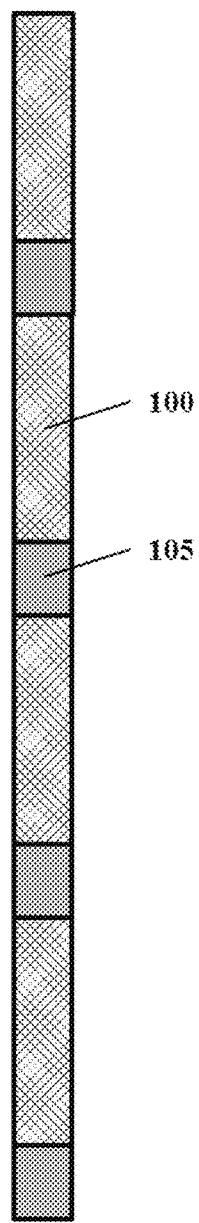
FIG. 5 illustrates a diagram of an embodiment of an embolization device, in accordance with the present disclosure.

Turning to FIG. 5, in some embodiments, an embolization device may comprise a fiber section 100 which may comprise a plurality of polymeric electrospun fibers as described above, and optionally, one or more contrast agents. Optionally, a fiber section may further comprise one or more hydrophilic components. In one embodiment, the embolization device comprises fiber sections and excludes a core structure, which may comprise metal or a polymer, within the fiber sections. FIG. 2 illustrates an embodiment of a twisted sheet of polymeric electrospun fibers in accordance with the present disclosure. FIG. 3A and FIG. 3B are scanning electron microscope (SEM) images illustrating the differences between a standard platinum coil (FIG. 3A) and a fiber section as described herein (FIG. 3B).

In certain embodiments, a fiber section may comprise polymeric electrospun fibers that have been twisted together, while in other embodiments, a fiber section may comprise one or more polymeric electrospun fibers that have not been twisted together. In some embodiments, a fiber section may comprise a sheet of polymeric electrospun fibers.

Figure 4:
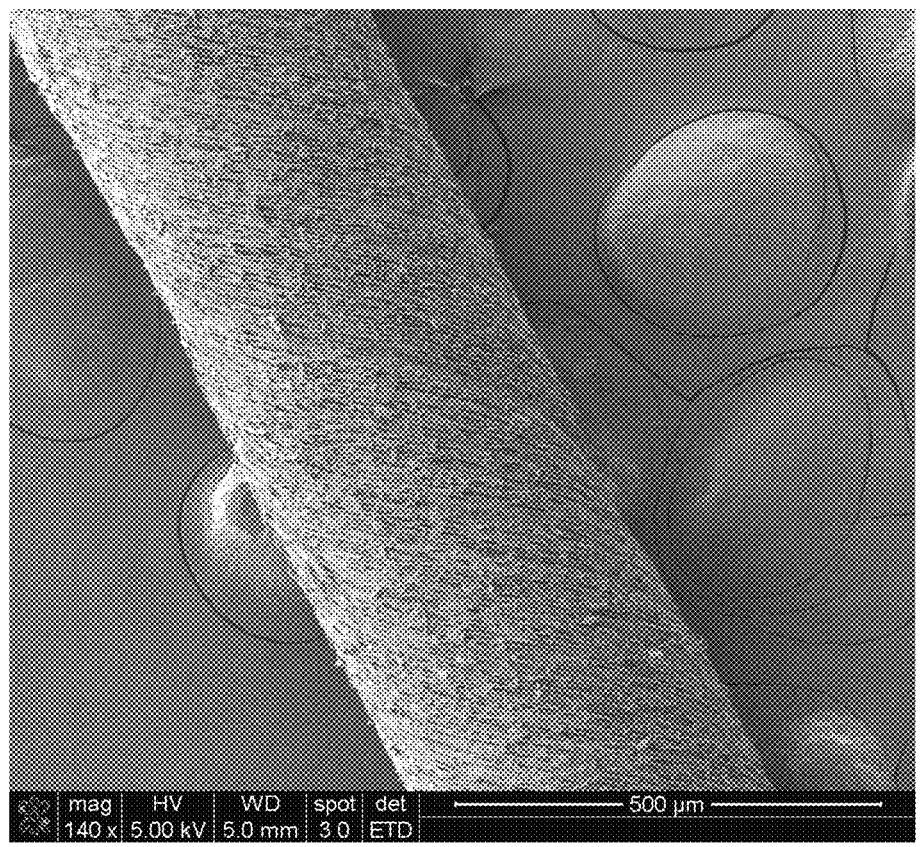
FIG. 4 illustrates another embodiment of a twisted fiber section in accordance with the present disclosure.

The fiber section may, in some aspects, may comprise a twisted sheet of polymeric electrospun fibers, as shown in FIG. 3B and FIG. 4. The sheet may have, for example, a uniform or varied thickness, and a uniform shape such as a rectangle or trapezoid, or a non-uniform shape. In some embodiments, the fiber section may comprise from about 200 twists per meter to about 4000 twists per meter. In some embodiments, the fiber section may comprise, for example, about 200 twists per meter, about 225 twists per meter, about 250 twists per meter, about 275 twists per meter, about 300 twists per meter, about 325 twists per meter, about 350 twists per meter, about 375 twists per meter, 400 twists per meter, about 425 twists per meter, about 450 twists per meter, about 475 twists per meter, about 500 twists per meter, about 525 twists per meter, about 550 twists per meter, about 575 twists per meter, about 600 twists per meter, about 625 twists per meter, about 650 twists per meter, about 675 twists per meter, about 700 twists per meter, about 725 twists per meter, about 750 twists per meter, about 775 twists per meter, about 800 twists per meter, about 825 twists per meter, about 850 twists per meter, about 875 twists per meter, about 900 twists per meter, about 925 twists per meter, about 950 twists per meter, about 975 twists per meter, about 1000 twists per meter, about 1025 twists per meter, about 1050 twists per meter, about 1075 twists per meter, about 1100 twists per meter, about 1125 twists per meter, about 1150 twists per meter, about 1175 twists per meter, about 1200 twists per meter, about 1225 twists per meter, about 1250 twists per meter, about 1275 twists per meter, about 1300 twists per meter, about 1325 twists per meter, 1350 twists per meter, about 1375 twists per meter, about 1400 twists per meter, about 1425 twists per meter, 1450 twists per meter, about 1475 twists per meter, about 1500 twists per meter, about 1525 twists per meter, about 1550 twists per meter, about 1575 twists per meter, about 1600 twists per meter, about 1625 twists per meter, about 1650 twists per meter, about 1675 twists per meter, about 1700 twists per meter, about 1725 twists per meter, about 1750 twists per meter, about 1775 twists per meter, about 1800 twists per meter, about 1825 twists per meter, about 1850 twists per meter, about 1875 twists per meter, about 1900 twists per meter, about 1925 twists per meter, about 1950 twists per meter, about 1975 twists per meter, about 2000 twists per meter, 2025 twists per meter, about 2050 twists per meter, about 2075 twists per meter, about 2100 twists per meter, about 2125 twists per meter, about 2150 twists per meter, about 2175 twists per meter, about 2200 twists per meter, about 2225 twists per meter, about 2250 twists per meter, about 2275 twists per meter, about 2300 twists per meter, about 2325 twists per meter, 2350 twists per meter, about 2375 twists per meter, about 2400 twists per meter, about 2425 twists per meter, 2450 twists per meter, about 2475 twists per meter, about 2500 twists per meter, about 2525 twists per meter, about 2550 twists per meter, about 2575 twists per meter, about 2600 twists per meter, about 2625 twists per meter, about 2650 twists per meter, about 2675 twists per meter, about 2700 twists per meter, about 2725 twists per meter, about 2750 twists per meter, about 2775 twists per meter, about 2800 twists per meter, about 2825 twists per meter, about 2850 twists per meter, about 2875 twists per meter, about 2900 twists per meter, about 2925 twists per meter, about 2950 twists per meter, about 2975 twists per meter, about 3000 twists per meter, 3025 twists per meter, about 3050 twists per meter, about 3075 twists per meter, about 3100 twists per meter, about 3125 twists per meter, about 3150 twists per meter, about 3175 twists per meter, about 3200 twists per meter, about 3225 twists per meter, about 3250 twists per meter, about 3275 twists per meter, about 3300 twists per meter, about 3325 twists per meter, 3350 twists per meter, about 3375 twists per meter, about 3400 twists per meter, about 3425 twists per meter, 3450 twists per meter, about 3475 twists per meter, about 3500 twists per meter, about 3525 twists per meter, about 3550 twists per meter, about 3575 twists per meter, about 3600 twists per meter, about 3625 twists per meter, about 3650 twists per meter, about 3675 twists per meter, about 3700 twists per meter, about 3725 twists per meter, about 3750 twists per meter, about 3775 twists per meter, about 3800 twists per meter, about 3825 twists per meter, about 3850 twists per meter, about 3875 twists per meter, about 3900 twists per meter, about 3925 twists per meter, about 3950 twists per meter, about 3975 twists per meter, about 4000 twists per meter, or ranges between any two of these values, including endpoints. In one embodiment, the fiber section may comprise about 531 twists per meter. In another embodiment, the fiber section may comprise about 1067 twists per meter.

The thickness of the fiber section may be from about 15 μm to about 500 μm. In some embodiments, the thickness of the fiber section may be, for example, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 125 μm, about 150 μm, about 175 μm, about 200 μm, about 225 μm, about 250 μm, about 275 μm, about 300 μm, about 325 μm, about 350 μm, about 375 μm, about 400 μm, about 425 μm, about 450 μm, about 475 μm, about 500 μm, or ranges between any two of these values, including endpoints.

FIG. 5 illustrates a diagram of an embodiment of an embolization device, in accordance with the present disclosure. In some embodiments, each fiber section 100 may range in length from about 5 mm to about 500 mm. In some non-limiting examples, the length of the fiber sections may be about 5 mm, about 10 mm, about 20 mm, about 30 mm, about 40 mm, about 50 mm, about 60 mm, about 70 mm, about 80 mm, about 90 mm, about 100 mm, about 200 mm, about 300 mm, about 400 mm, about 500 mm, or ranges between any two of these values, including endpoints.

In some embodiments, each fiber section 100 may have a width ranging from about 5 mm to about 500 mm. In some non-limiting examples, the width of each fiber section may be about 5 mm, about 10 mm, about 20 mm, about 30 mm, about 40 mm, about 50 mm, about 60 mm, about 70 mm, about 80 mm, about 90 mm, about 100 mm, about 200 mm, about 300 mm, about 400 mm, about 500 mm, or ranges between any two of these values, including endpoints.

In some embodiments, each fiber section 100 may have a stiffness ranging from about 0.01 g to about 10 g to reflect the distal 1 cm of the tip of the fiber section. In some non-limiting examples, the stiffness of each fiber section may be about 0.01 g, about 0.02 g, about 0.03 g, about 0.04 g, about 0.05 g, about 0.06 g, about 0.07 g, about 0.08 g, about 0.09 g, about 0.1 g, about 0.2 g, about 0.3 g, about 0.4 g, about 0.5 g, about 0.6 g, about 0.7 g, about 0.8 g, about 0.9 g, about 1 g, about 2 g, about 3 g, about 4 g, about 5 g, about 6 g, about 7 g, about 8 g, about 9 g, about 10 g, or ranges between any two of these values, including endpoints. In one embodiment, the stiffness of a fiber section may be about 0.05 g. In another embodiment, the stiffness of a fiber section may be about 0.3 g.

Figure 6:
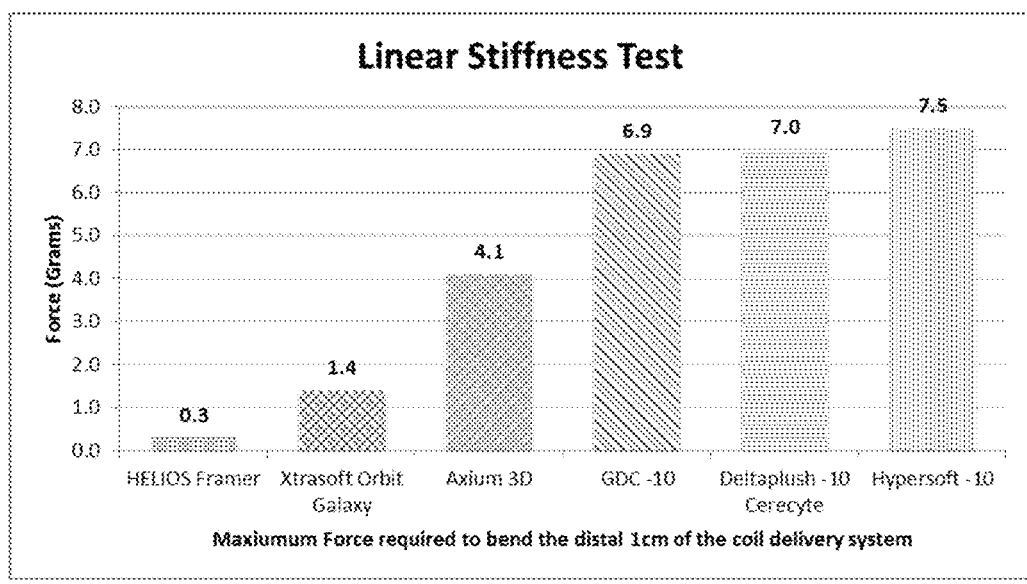
FIG. 6 illustrates linear deflection stiffness data, expressed as the maximum force in grams required to bend the distal 1 cm of an embodiment of an embolization device made in accordance with the present disclosure (labeled HELIOS), compared to the same measurement for other commercially available embolization devices.

FIG. 6 illustrates linear deflection stiffness data, expressed as the maximum force in grams required to bend the distal 1 cm of an embodiment of an embolization device made in accordance with the present disclosure (labeled HELIOS), compared to the same measurement for other commercially available embolization devices. The embodiment of the embolization device made in accordance with the present disclosure demonstrates significantly lower stiffness than a typical platinum embolization device.

Figure 7A:
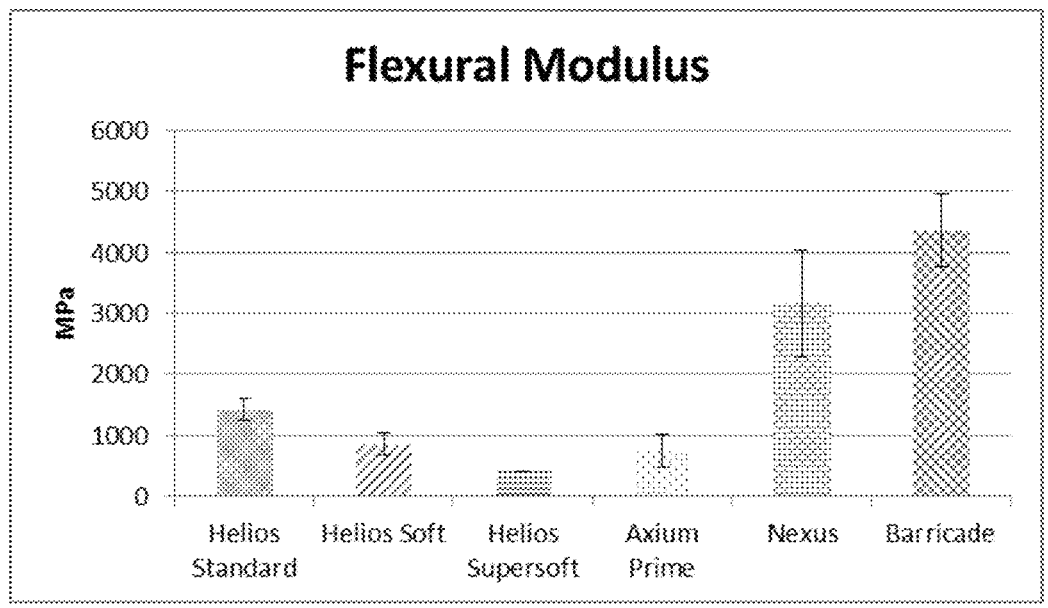
FIG. 7A illustrates flexural modulus data from the 3-point bending test of an embolization device in accordance with the present disclosure (labeled HELIOS), as compared to several commercially available coils.
Figure 7B:
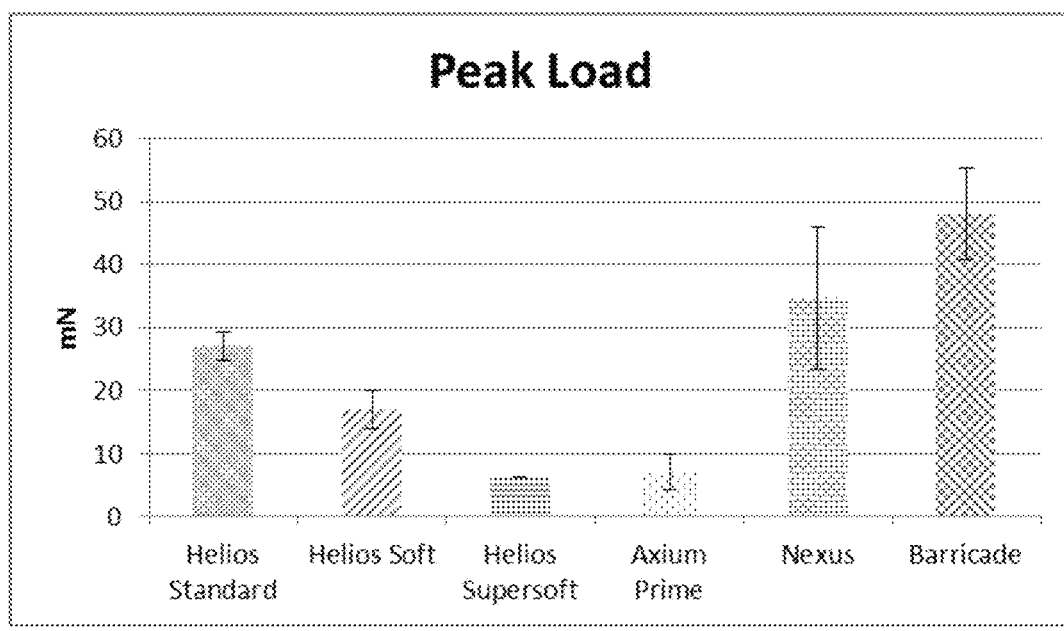
FIG. 7B illustrates peak load data from the 3-point bending test of an embolization device in accordance with the present disclosure (labeled HELIOS), as compared to several commercially available coils.

The stiffness of each fiber section may be also be described using an alternative stiffness test, such as a 3-point bending test. FIG. 7A and FIG. 7B illustrate flexural modulus and peak load, respectively, from the 3-point bending test of an embolization device in accordance with the present disclosure (labeled HELIOS), as compared to several commercially available coils. Importantly, the HELIOS devices demonstrated superior flexural modulus and peak load performance as compared to the other commercially available devices.

In some embodiments, each fiber section 100 may have a diameter ranging from about 100 µm to about 1000 µm. In some non-limiting examples, the diameter of each fiber section may be about 100 µm, about 110 µm, about 120 µm, about 130 µm, about 140 µm, about 150 µm, about 160 µm, about 170 µm, about 180 µm, about 190 µm, about 200 µm, 210 µm, about 220 µm, about 230 µm, about 240 µm, about 250 µm, about 260 µm, about 270 µm, about 280 µm, about 290 µm, about 300 µm, 310 µm, about 320 µm, about 325 µm, about 330 µm, about 340 µm, about 350 µm, about 360 µm, about 370 µm, about 380 µm, about 390 µm, about 400 µm, 410 µm, about 420 µm, about 430 µm, about 440 µm, about 450 µm, about 460 µm, about 470 µm, about 480 µm, about 490 µm, about 500 µm, 510 µm, about 520 µm, about 530 µm, about 540 µm, about 550 µm, about 560 µm, about 570 µm, about 580 µm, about 590 µm, about 600 µm, 610 µm, about 620 µm, about 630 µm, about 640 µm, about 650 µm, about 660 µm, about 670 about 680 µm, about 690 µm, about 700 µm, 710 µm, about 720 µm, about 730 µm, about 740 µm, about 750 µm, about 760 µm, about 770 µm, about 780 µm, about 790 µm, about 800 µm, 810 µm, about 820 µm, about 830 µm, about 840 µm, about 850 µm, about 860 µm, about 870 µm, about 880 µm, about 890 µm, about 900 µm, 910 µm, about 920 µm, about 930 µm, about 940 µm, about 950 µm, about 960 µm, about 970 µm, about 980 µm, about 990 µm, about 1000 µm, or ranges between any two of these values, including endpoints. In one embodiment, the diameter of the fiber section may be about 330 µm. In another embodiment, the diameter of the fiber section may be about 360 µm.

In some embodiments, the contrast agent which may be included in the fiber section 100 may allow for the embolization device to be viewed and monitored with standard radiological imaging techniques, such as, for example, fluoroscopic imaging, during and following its insertion into a vessel. In some embodiments, the contrast agent may be, for example, bismuth, bismuth (III) oxide, barium, tungsten, iodine, gadolinium, gold, platinum, tantalum, gadolinium, diatrizoate, metrizoate, ioxaglate, iopamidol, iohexol, ioxilan, iopromide, iodixanol, or any combination thereof.

In some embodiments, the hydrophilic component which may be included in the fiber section 100 may allow the embolization device to be more easily deployed by allowing it to pass easily though a catheter or other delivery vehicle 115. In some embodiments, the hydrophilic component may allow the fiber section 100 to volumetrically expand beyond its original dimensions to allow for greater packing densities than a similar device without a hydrophilic component may exhibit. In some embodiments, the hydrophilic component may be, for example, a polyurethane.

Figure 8:
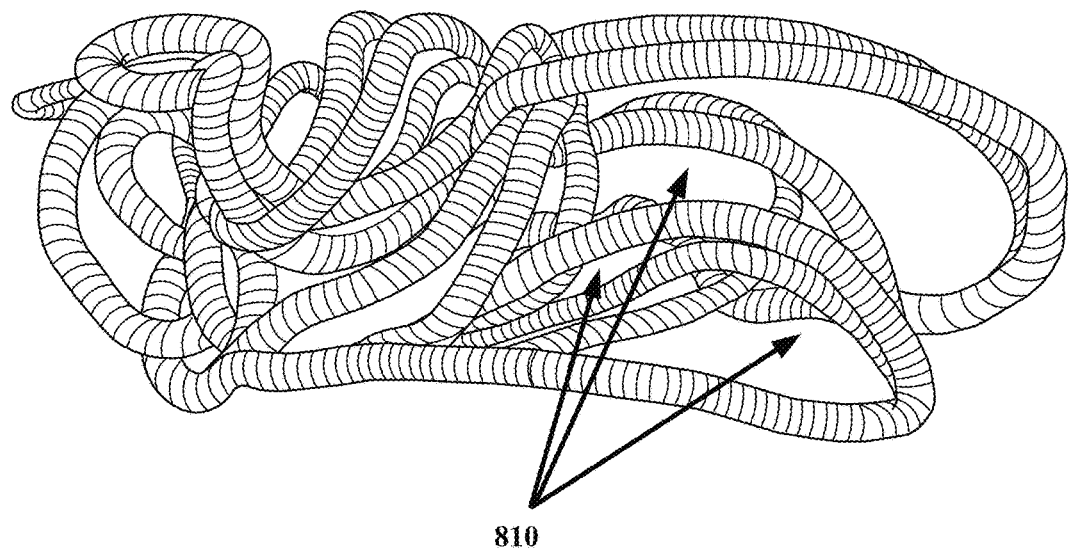
FIG. 8 illustrates a standard platinum coil within an animal model of an aneurysm, with a packing density of about 30% (as denoted by the gaps), and a lack of tissue regrowth within and around the aneurysm.
Figure 9:
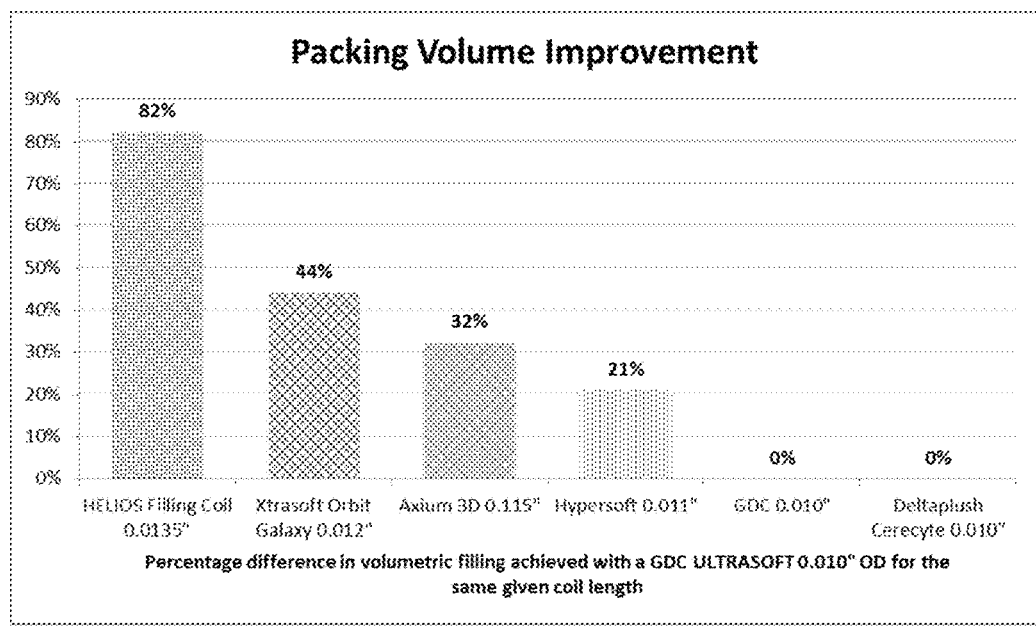
FIG. 9 illustrates packing volume improvement data, expressed as the percentage difference in volumetric filling, achieved with an embolization device made in accordance with the present disclosure (labeled HELIOS) compared to other commercially available embolization devices.

The packing density of an embolization device as described herein improves dramatically over that of a standard platinum coil. FIG. 8 illustrates a standard platinum coil within an aneurysm model. In particular, FIG. 8 clearly shows a packing density of about 30% (as denoted by the gaps 810), a lack of tissue regrowth within and around the aneurysm, and the protrusion of a loop of the platinum coil into the parent artery (not shown). In contrast to the packing density of the standard platinum coil, as shown in FIG. 8, FIG. 9 illustrates packing volume improvement data, expressed as the percentage difference in volumetric filling achieved with a standard comparator (labeled GDC) for the same given coil length. Data for an embolization device made in accordance with the present disclosure (labeled HELIOS) is compared to the same measurement for other commercially available embolization devices.

In some embodiments, the embolization device may range in length from about 5 mm to about 100 cm. In some non-limiting examples, the length of the embolization device may be about 5 mm, about 10 mm, about 20 mm, about 30 mm, about 40 mm, about 50 mm, about 60 mm, about 70 mm, about 80 mm, about 90 mm, about 100 mm, about 200 mm, about 300 mm, about 400 mm, about 500 mm, about 600 mm, about 700 mm, about 800 mm, about 900 mm, about 100 cm, or ranges between any two of these values, including endpoints.

In some embodiments, an embolization device may further include a plurality of fiber sections 100 as described above, wherein each fiber section is separated by an electrolytically degradable linker 105. In some embodiments, multiple linkers 105 may be positioned along the device in an alternating fashion with the fiber sections 100, as shown in FIG. 5. In some embodiments, the linker 105 may comprise two metals having different galvanic potentials. In some embodiments, the two metals having different galvanic potentials may be connected such that the end of a first metal is melted to the end of a second metal. In some embodiments, the linker 105 may comprise an electrically conductive degradable polymer blend. In some embodiments, the inclusion of one or more linkers 105 between fiber sections 100 may allow the user to choose a custom length of the embolization device during the insertion portion of the procedure, as compared to having to make an educated guess prior to insertion of the device, or having to continually add additional components of the device during the procedure. An embolization device comprising fiber sections 100 separated by one or more linkers 105 may allow the user to use a device which is longer than needed. The user may insert the embolization device into a vessel until the desired degree of packing is reached. The linker 105 may then be separated using an electrical current, and the excess embolization device may be retracted through a delivery vehicle 115. In some embodiments, linkers 105 may range in length from about 0.1 mm to about 10 mm. In some non-limiting examples, the length of the linkers may be about 0.1 mm, about 0.5 mm, about 1 mm, about 2 mm, about 3 mm, about 4 mm, about 5 mm, about 6 mm, about 7 mm, about 8 mm, about 9 mm, about 10 mm, or ranges between any two of these values, including endpoints.

Figure 10A:
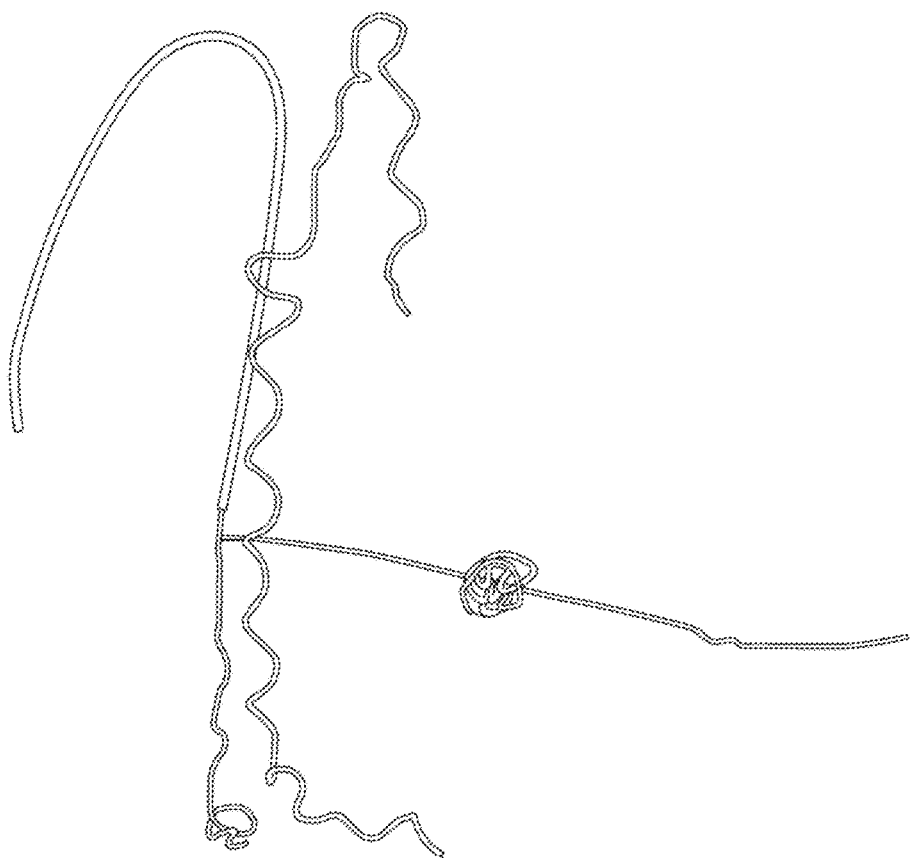
FIG. 10A illustrates an embodiment of a fully shaped fiber section in accordance with the present disclosure.
Figure 10B:
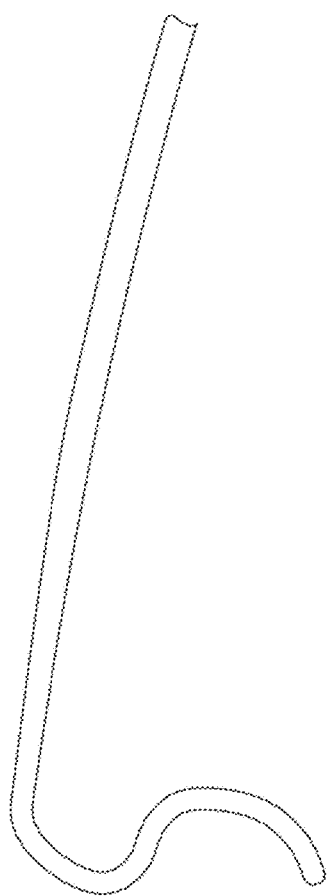
FIG. 10B illustrates an embodiment of an S-shaped tip of a fiber section, in accordance with the present disclosure.
Figure 10C:
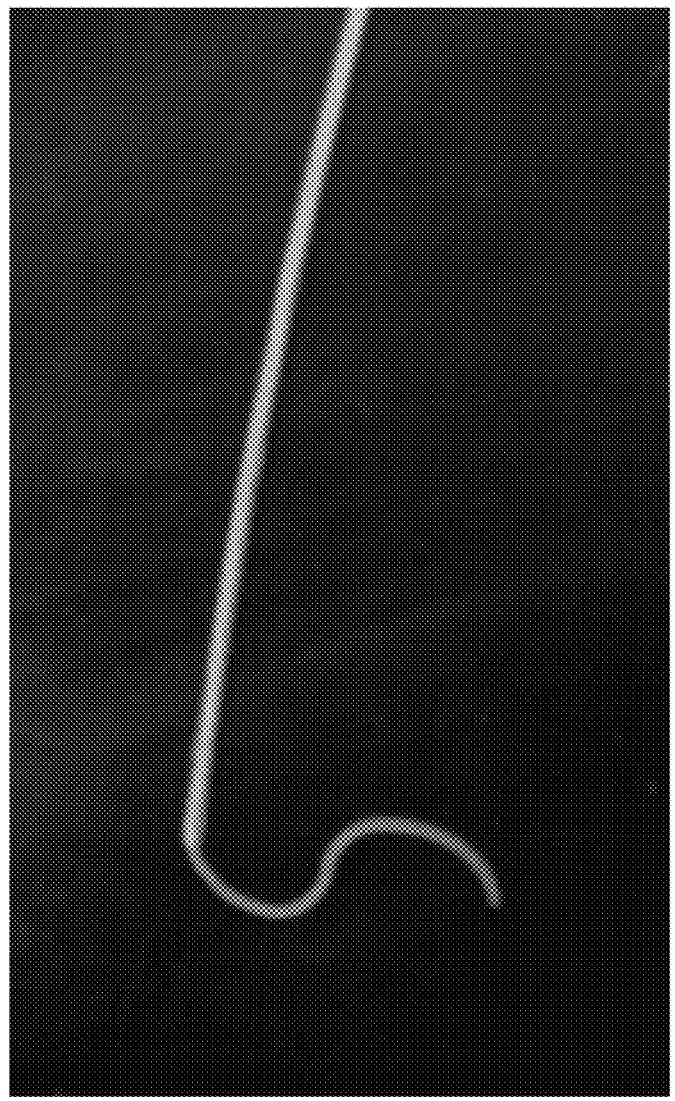
Figure 10D:
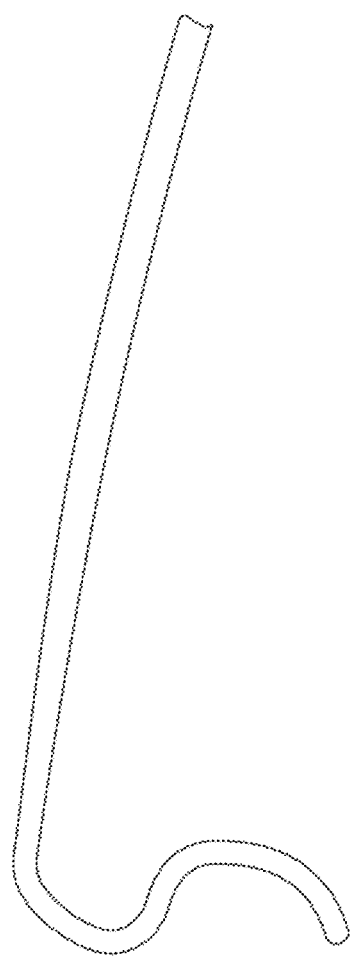

In some embodiments, the embolization device may be at least partially formed into a shape. In some aspects, the shape may be spherical, helical, conical, sinusoidal, J-shaped, S-shaped, shepherd's hook shaped, L-shaped, straight tail shaped, Omega-shaped, or any combination thereof. FIG. 10A illustrates an embodiment of a fully shaped fiber section in accordance with the present disclosure. FIG. 10B illustrates an embodiment of an S-shaped tip of a fiber section, in accordance with the present disclosure.

In some embodiments, the embolization device may further include a delivery vehicle. The delivery vehicle may be adhered, affixed, or secured to at least a portion of the embolization device, for example with an adhesive, such as an adhesive comprising polycaprolactone and dichloromethane, or the embolization device may looped, coiled, or otherwise shaped around or inserted into the delivery vehicle.

Figure 11:
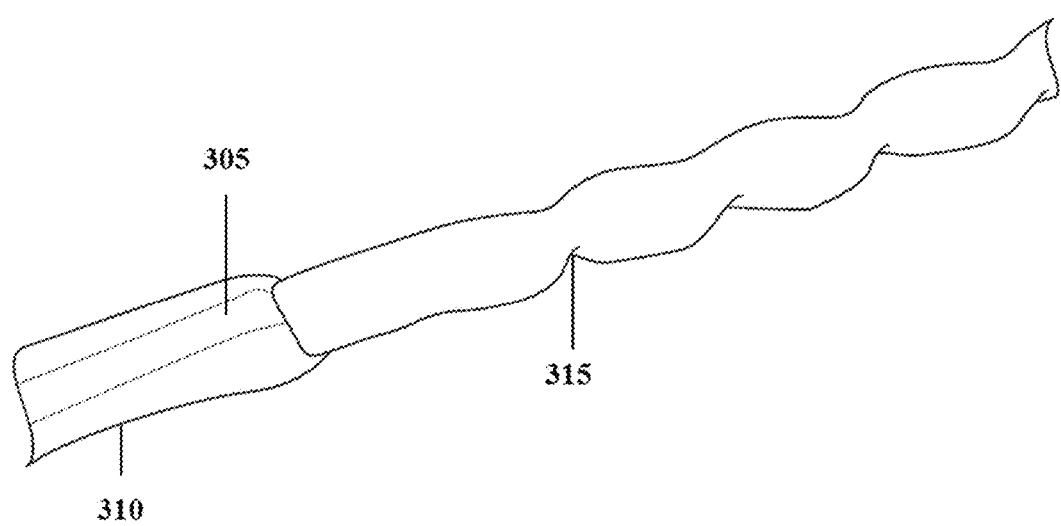
FIG. 11 illustrates an embodiment of a delivery vehicle, a sheath, and a crimped fiber section, in accordance with the present disclosure.

In some embodiments, the delivery vehicle may comprise an inner wire 305 and an outer sheath 310, with the inner wire 305 offset from the central axis of the outer sheath 310 by a distance of about 1 mm to about 10 mm, as illustrated in FIG. 11. The distance may be, for example, about 1 mm, about 2 mm, about 3 mm, about 4 mm, about 5 mm, about 6 mm, about 7 mm, about 8 mm, about 9 mm, about 10 mm, or any range between any two of these values, including endpoints. At least a portion of the embolization device, for example, a fiber portion, may be located in the outer sheath 310 of the delivery vehicle. The outer sheath 310 may, in some embodiments, comprise at least one crimp 315 having a depth, the crimp 315 configured to stabilize the portion of the embolization device within the outer sheath. In some embodiments, the outer sheath may comprise from about 1 crimp to about 100 crimps. The outer sheath 310 may comprise, for example, about 1 crimp 315, about 2 crimps, about 3 crimps, about 4 crimps, about 5 crimps, about 6 crimps, about 7 crimps, about 8 crimps, about 9 crimps, about 10 crimps, about 15 crimps, about 20 crimps, about 25 crimps, about 30 crimps, about 35 crimps, about 40 crimps, about 45 crimps, about 50 crimps, about 55 crimps, about 60 crimps, about 65 crimps, about 70 crimps, about 75 crimps, about 80 crimps, about 85 crimps, about 90 crimps, about 95 crimps, about 100 crimps, or any range between any two of these values, including endpoints.

In some embodiments, the depth of the crimp may be from about 0.001 inches to about 0.1 inches. The depth may be, for example, about 0.001 inches, 0.002 inches, 0.003 inches, 0.004 inches, 0.005 inches, 0.006 inches, 0.007 inches, 0.008 inches, 0.009 inches, 0.01 inches, 0.02 inches, 0.03 inches, 0.04 inches, 0.05 inches, 0.06 inches, 0.07 inches, 0.08 inches, 0.09 inches, 0.1 inches, or any range between any two of these values, including endpoints.

Deploying the Embolization Device

A method of deploying an embolization device described herein may include inserting into a vessel an embolization device described herein.

Figure 12:
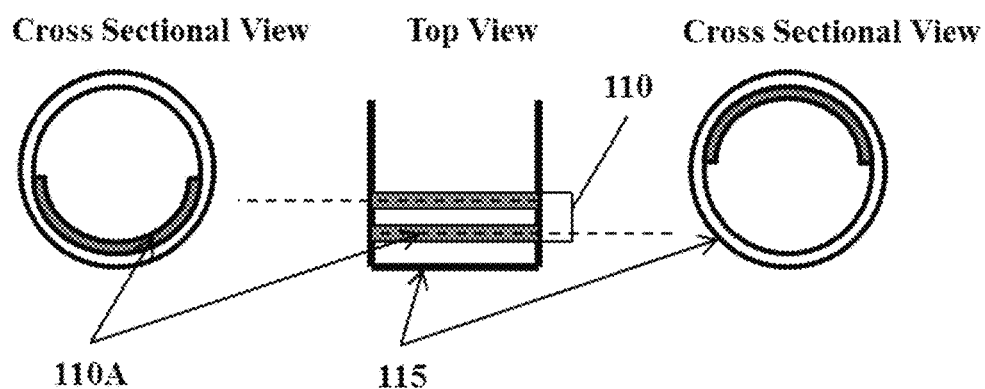
FIG. 12 illustrates a schematic diagram of an embodiment of an embolization device comprising two separate conducting electrical leads ending in two non-intersecting half-loops of conductive material, in accordance with the present disclosure.

In some embodiments, the method may further comprise applying an electrical current to one or more of the linkers. In some embodiments, an electrical current applicator 110 may be used to separate one or more linkers 105 from their adjacent fiber sections 100. In some embodiments, the electrical current applicator 110 may comprise two separate conducting electrical leads ending in two non-intersecting half-loops 110A of conductive material, as shown in FIG. 12. In some embodiments, the conductive material may comprise, for example, copper, aluminum, silver, or gold.

Figure 13:
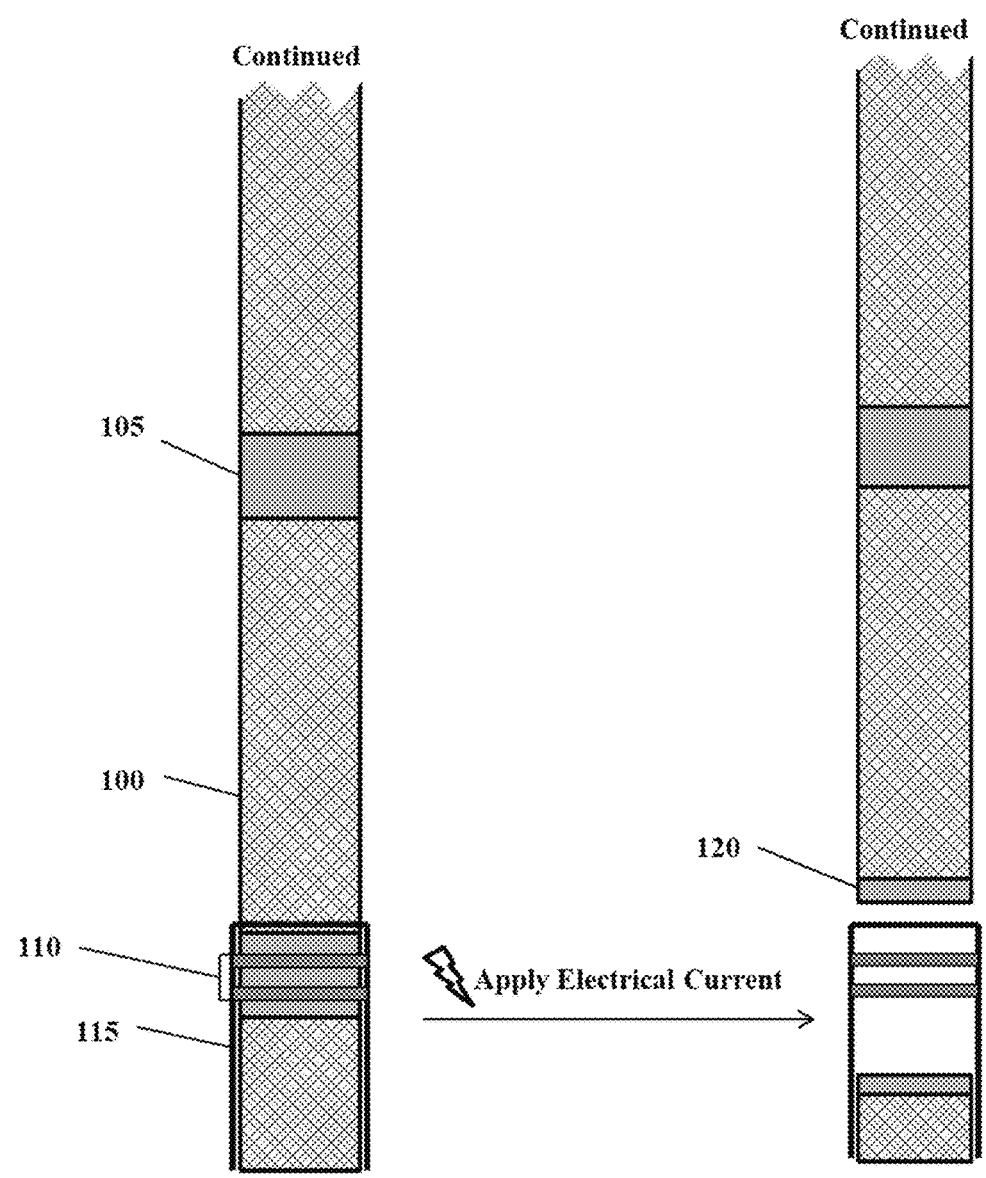
FIG. 13 illustrates a schematic diagram of an intact embolization device prior to the application of an electrical current on the left, followed by the same embolization device with a linker having been separated by application of the electrical current on the right.

In some embodiments, a linker 105 may be broken by situating the linker 105 such that it is in electrical communication with the electrical current applicator 110, and passing a current through the linker 105, as shown schematically in FIG. 13. In some embodiments, the electrical current may travel from one half-loop 110A to the other half loop through the linker 105, inducing electrolysis only in the linker 105 in electrical communication with the electrical current applicator 110. In some embodiments, such electrolysis may be isolated due to the insulating properties of the fiber sections 100. In some embodiments, the electrical current applicator 110 may be positioned at the end of a delivery vehicle 115 to ensure that the electrical current applicator 110 is located near the linker 105 that will need to be broken during the deployment of the embolization device. In some embodiments, a linker 105 to which an electrical current has been applied may leave behind a detached linker end 120. In some embodiments, a linker 105 may be completely dissolved after the application of an electrical current. In some embodiments, differing levels of radio-opacity between the fiber sections 100 and the linkers 105 may allow the user to easily position the electrical current applicator 110 at the appropriate linker 105.

In other embodiments, the method of deploying the embolization device may further comprise applying electrothermal heat to one or more of the linkers. At least a portion of the embolization device may be attached to the delivery device by an adhesive, such as one comprising polycaprolactone and dichloromethane, and the delivery vehicle may comprise a resistive or heating element. The delivery vehicle may further comprise a positive lead an a negative lead, each insulated from the other, and the leads may be exposed. To apply electrothermal heat to a portion of the embolization device, a controlled voltage may be applied across the two leads, such that a controlled or constant current may be achieved. The current may pass through the heating element, heating the delivery vehicle until the adhesive is at least partially melted, thereby releasing the embolization device. In such an embodiment, the melting point of the embolization device may be higher than the melting point of the adhesive.

In some embodiments, the electrical current applied to deploy the embolization device may range from about 0.1 mA to about 100 mA. The electrical current may be, for example, about 0.1 mA, about 0.5 mA, about 1 mA, about 2 mA, about 3 mA, about 4 mA, about 5 mA, about 6 mA, about 7 mA, about 8 mA, about 9 mA, about 10 mA, about 20 mA, about 30 mA, about 40 mA, about 50 mA, about 60 mA, about 70 mA, about 80 mA, about 90 mA, about 100 mA, or any range between any two of these values, including endpoints. In some embodiments, the electrical current may be 2 mA.

In other embodiments, the method of deploying the embolization device may further comprise applying force, such as a mechanical force, to at least a portion of a delivery vehicle having an inner wire and outer sheath, as described above and shown in FIG. 11. In such an embodiment, the force applied to the portion of the delivery vehicle serves to release the embolization device from the crimped portion of the outer sheath, thereby releasing it into the desired location.

Processing the Fiber Section

A method of manufacturing an embolization device may comprise electrospinning at least one polymer, as described herein and known in the art, to form a fiber section having an original length, and processing the fiber section.

In some embodiments, processing the fiber section may comprise applying a strain in order to increase its stiffness. In one embodiment, the strain may be about 25% of the original length of the fiber section, wherein strain is equal to the change in length divided by the original length. In another embodiment, the strain may be about 50% of the original length of the fiber section. In another embodiment, the strain may be about 100% of the original length of the fiber section. In still another embodiment, the strain may be about 200% of the original length of the fiber section. In some non-limiting examples, the strain may be about 10% of the original length of the fiber section, about 20% of the original length of the fiber section, about 25% of the original length of the fiber section, about 30% of the original length of the fiber section, about 40% of the original length of the fiber section, about 50% of the original length of the fiber section, about 60% of the original length of the fiber section, about 70% of the original length of the fiber section, about 75% of the original length of the fiber section, about 80% of the original length of the fiber section, about 90% of the original length of the fiber section, about 100% of the original length of the fiber section, or ranges between any two of these values, including endpoints.

In some embodiments, processing the fiber section may comprise twisting it to produce a range of twists per meter, as described above. The fiber section may be twisted, for example, by attaching one end to a motor and the other end to a fixed position, or by attaching each end to a separate motor. In such embodiments, the motor(s) will rotate and apply a range of twists per meter to the fiber section. Increasing the number of twists per meter serves to increase the stiffness and decrease the diameter of the fiber section.

In some embodiments, processing the fiber section may comprise shaping it into any of the shapes described herein and shown in FIG. 10A and FIG. 10B, or any equivalents thereof. The shaping may be done, for example, by wrapping a fiber section around a shaped surface. The shaping may also be done by a medical professional prior to inserting the fiber section into a vessel.

In some embodiments, processing the fiber section may comprise applying heat to, or "heat setting" the fiber section. Heat may be applied independent of the other processing steps described, or may be applied after one or more of the processing steps described, such as straining, twisting, and shaping, in order to set the shape of the strained, twisted, or shaped fiber portion. In some embodiments, heating the fiber section may comprise heating it to a temperature below the melting point of at least one of the polymer fibers within the fiber section for a length of time. The temperature may be, for example, from about 150° F. to about 400° F. In some non-limiting examples, the temperature may be about 150° F., about 175° F., about 185° F., about 190° F., about 200° F., about 225° F., about 250° F., about 275° F., about 300° F., about 325° F., about 350° F., about 375° F., about 400° F., or any range between any two of these values, including endpoints. The length of time may be, for example, from about 1 minute to about 60 minutes. In some non-limiting examples, the length of time may be about 1 minute, about 2 minutes, about 3 minutes, about 4 minutes, about 5 minutes, about 6 minutes, about 7 minutes, about 8 minutes, about 9 minutes, about 10 minutes, about 12 minutes, about 15 minutes, about 18 minutes, about 20 minutes, about 25 minutes, about 30 minutes, about 35 minutes, about 40 minutes, about 45 minutes, about 50 minutes, about 55 minutes, about 60 minutes, or any range between any two of these values, including endpoints.

Examples of Applications

In some embodiments, the polymeric electrospun fibers may present a high degree of flexibility, allowing the embolization device to conform to the shape of a vessel or abnormality safely, resulting in a reduced risk of vessel rupture from device insertion. In some embodiments, the polymeric electrospun fibers may provide a high surface area interface upon which thrombosis may be initiated or may take place. In some aspects, the embolization device described herein may encourage cell ingrowth, and may provide a scaffold to encourage vessel healing once inserted. Without wishing to be bound by theory, in some embodiments the embolization device may create an optimal bed for tissue growth by promoting the migration and repopulation of endothelial cells.

In some embodiments, an embolization device may be used to treat or prevent pathologies such as, for example, an aneurysm, a parent vessel occlusion, a carotid venous fistula, an arteriovenous malformation, or any other vessel malformation or other pathology that may benefit from embolization.

The embolization device described herein may be formed for a number of different types of applications. In some of the pathologies described above, it may be advantageous to use both a longer, stiffer device, referred to as a "framing" device, alone or in combination with a shorter, softer device, referred to as a "filling" device. In some applications, a medical professional may use a framing device to first insert into the vessel, essentially outlining the space to be filled. The medical professional may then, in some cases, use the filling devices to fill the space defined, at least partially, by the framing device.

Figure 14A:
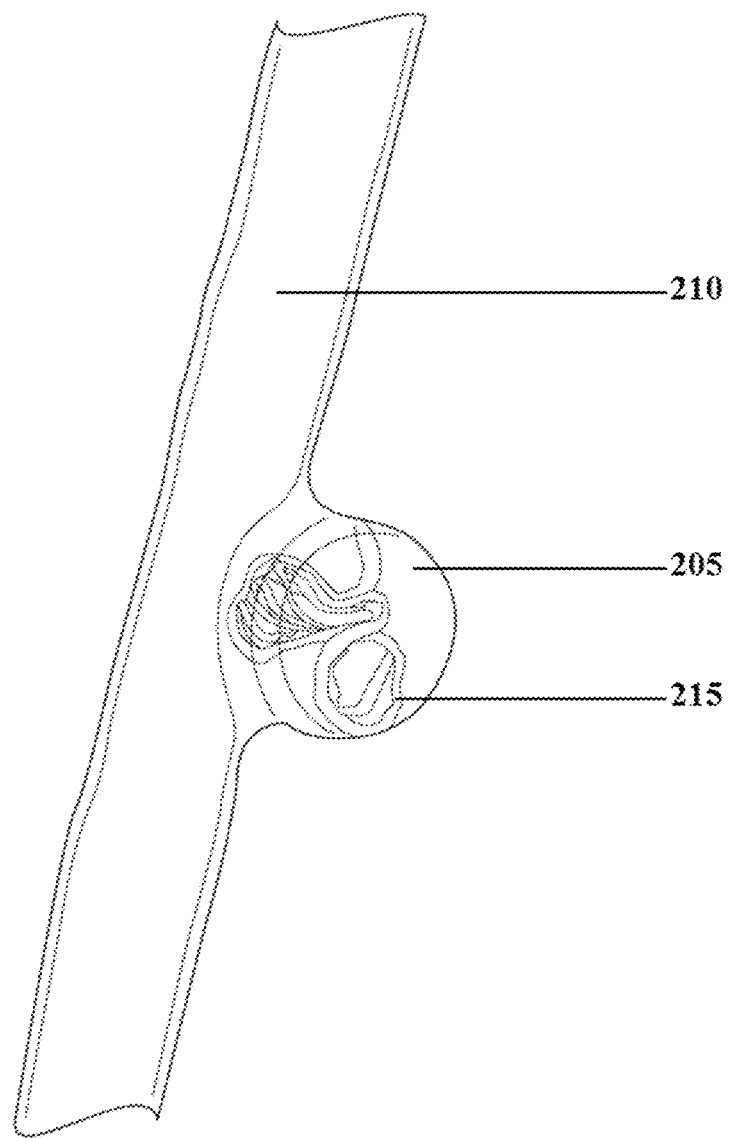
FIG. 14A illustrates an embodiment of an embolization device, in accordance with the present disclosure, within a model of an aneurysm.
Figure 14B:
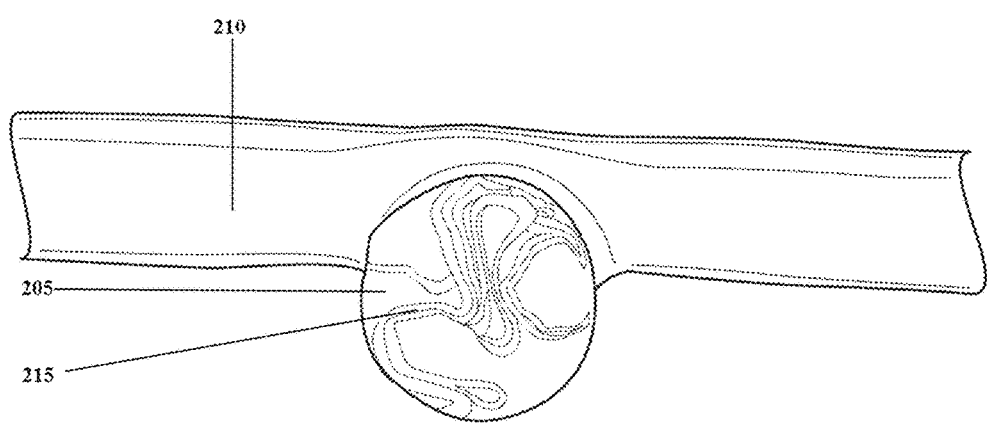
FIG. 14B illustrates an embodiment of an embolization device, in accordance with the present disclosure, within a model of an aneurysm.
Figure 14C:
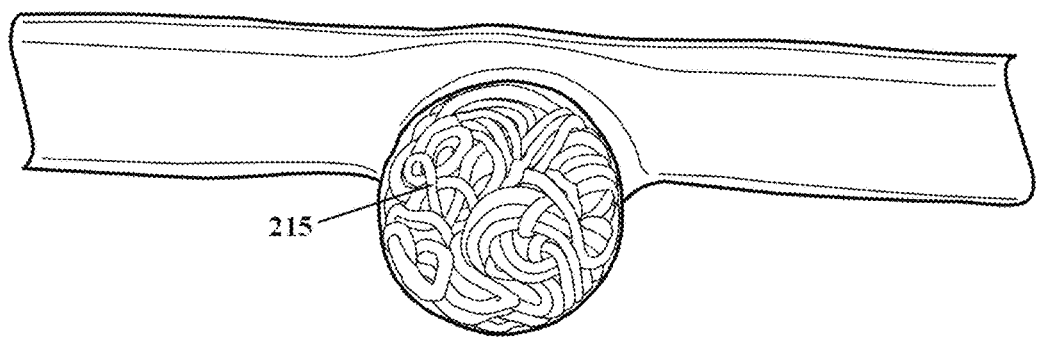
FIG. 14C illustrates an embodiment of an embolization device with a packing density of about 69% in the model aneurysm, in accordance with the present disclosure.
Figure 14D:
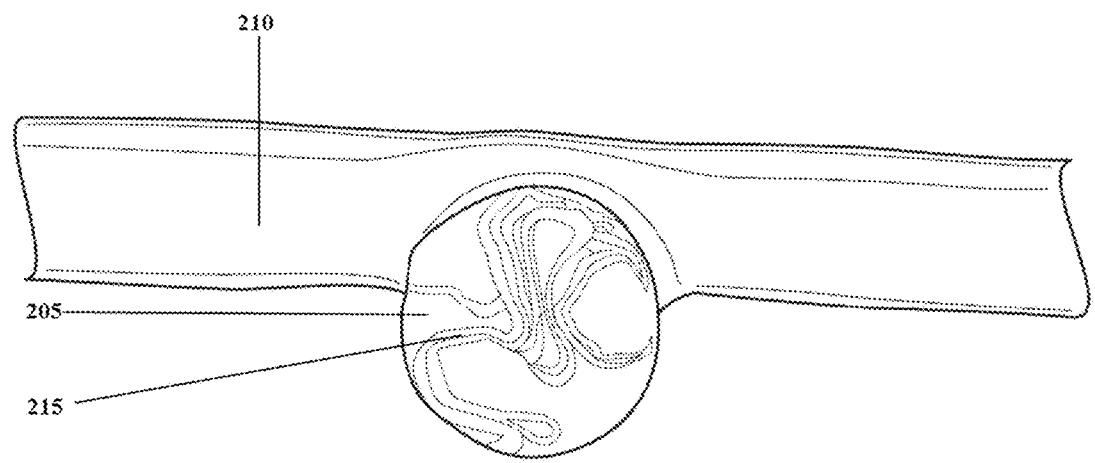
Figure 14E:
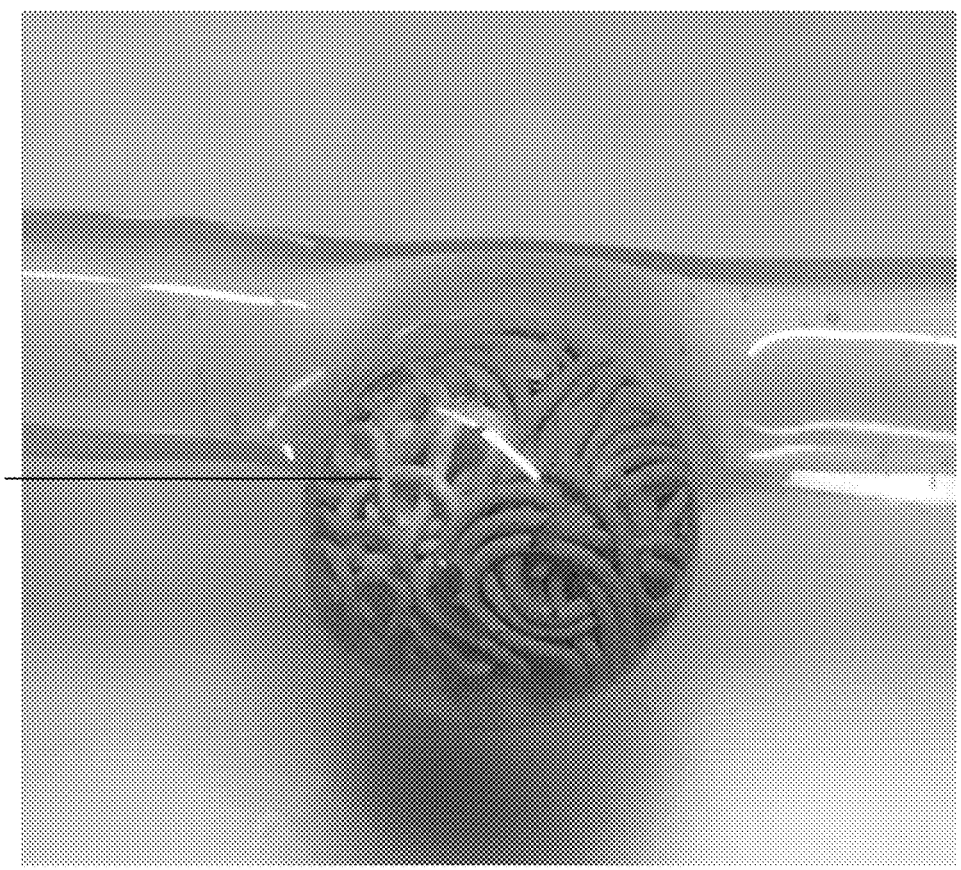
Figure 15A:
FIG. 15A illustrates the healing of a rabbit model of an aneurysm 30 days after embolization with a device and method according to the present disclosure. In contrast.
Figure 15B:
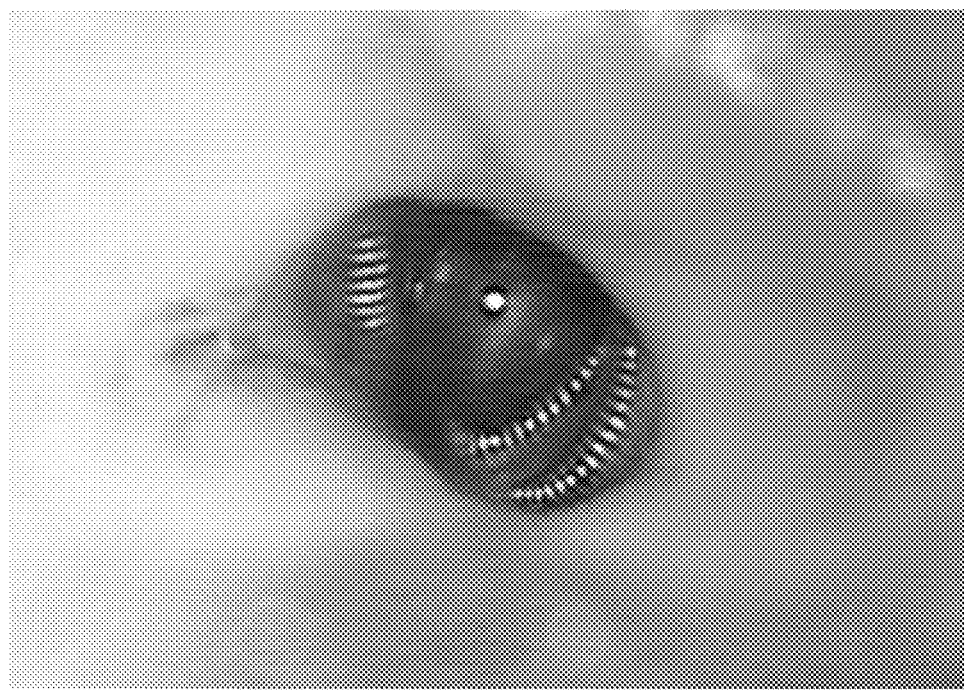
FIG. 15B illustrates vessel healing 30 days after embolization with a standard platinum coil.

FIG. 14A and FIG. 14B illustrate an embodiment of an embolization device 215, in accordance with the present disclosure, within a model of an aneurysm 205 and a parent vessel 210. In particular, FIG. 14A and FIG. 14B illustrate a model of an aneurysm 215 at an early stage of deploying the embolization device as described herein. FIG. 14A and FIG. 14B illustrate the embolization device 215 as it first enters the aneurysm 215, rather than the final stage of deployment, which would have a much higher packing density. FIG. 14C illustrates an embodiment of an embolization device 215, including "framing" and "filling" components as described above, with a packing density of about 69% in the model aneurysm, in accordance with the present disclosure. FIG. 15A illustrates the healing of a rabbit model of an aneurysm 30 days after embolization with a device and method according to the present disclosure, wherein nearly full healing can been seen. In contrast, FIG. 15B illustrates vessel healing 30 days after embolization with a standard platinum coil, wherein gaps, scarring, and generally poor healing can be seen.

Example: In Vivo Model

Study Design

An aneurysm model was used to compare an embolization device and method as described herein with a standard platinum coil. Ten New Zealand White rabbits were used during this study. Eight "experimental" rabbits were selected to receive an embolization device as described herein, by a method in accordance with the present disclosure. The remaining two "control" rabbits received platinum coils commonly known in the art.

Aneurysm Formation

At the outset, all ten animals were anesthetized, and each rabbit's right common carotid artery (CCA) was surgically exposed. A small arteriotomy was performed, and a 3-French vascular sheath was then advanced into the mid-portion of the CCA. A 3-French Fogarty balloon catheter was introduced, under fluoroscopic guidance, into the right CAA, and then placed within the braciocephalic artery at the most proximal part of the CCA. Then, a Prowler 10 microcatheter was placed upon the inflated balloon, and 100 U of porcine elastase was injected via the microcatheter to ensure high elastase concentration at the site. Later, the balloon catheter was used to increase the width of the aneurysm dome. Then, the balloon catheter, microcatheter, and sheath were removed. The CAA was ligated at its beginning. The skin of each animal was then closed with a running suture and surgical glue.

Embolization

After at least 4 weeks of healing time after the aneurysm formation, the animals were again anesthetized. The largest possible introducer sheath was placed in the femoral artery of each animal, using a percutaneous technique. The sheath was secured in place as necessary, and was flushed with sterile 0.9% sodium chloride. A baseline angiogram of the aneurysm was obtained, and the aneurysm neck width and fundus dimensions were measured.

A guide wire was then tracked into the aneurysm, and the catheter used for the baseline angiogram was removed. A microcatheter was then tracked over the guide wire, and the position of each was verified. In the eight "experimental" rabbits, a "framing" device in accordance with the present disclosure, with dimensions suitable for each aneurysm, was then selected. In the two "control" rabbits, a standard platinum coil was selected. In each case, the guide wire was then gently removed from the microcatheter, and either the "framing" device or the platinum coil was placed into the microcatheter. Either the "framing" device or the platinum coil was then gently pushed out of the microcatheter into the aneurysm, ensuring that no device or coil was left protruding out of the aneurysm neck into the parent vessel. Either the "framing" device or the platinum coil was then detached using its associated detachment system. This process was repeated—using additional "framing" and "filling" devices in accordance with the present disclosure in the "experimental" animals, and additional platinum coils in the "control" animals—until the aneurysm was filled. A final angiogram was run in each case to ensure the desired aneurysm occlusion rate. The microcatheter was then removed, and the incision was sutured.

Euthanasia and Harvest

Once the ten rabbits recovered from the procedure, they were maintained for 30 days, and then were euthanized according to standard protocol. After euthanasia, the artery with the created and occluded aneurysm in each animal was cut down with sufficient length proximal and distal to the implanted device for reference purposes. Each artery was then placed in a container and covered with a 10% formalin solution. Prior to processing for histology, the arteries were photographed and imaged by capturing high contrast digital-based radiographs to assess the location of each implanted device.

Light Microscopy

All aneurysm samples were dehydrated in a graded series of ethanol and embedded in Spurr's resin. After polymerization of the blocks, images were recorded and sample orientation was verified. The blocks were then sectioned on a rotary microtome in a coronal orientation, permitting long-axis sectioning of the aneurysm neck. Sections were cut on a rotary microtome at 4-6 µm and stained with H&E and Movat's Pentachrome. Cuts were made in a coronal plane along the long axis of the vessel to include a profile of the embolic device, sac wall, aneurysm neck, and some of the parent vessel lumen. Light microscopy changes were assessed according to the scores described in Table 1 below.

TABLE 1

| Parameters | 0 (none) | 1 (minimal) | 2 (mild) | 3 (moderate) | 4 (marked) |
|---|---|---|---|---|---|
| Neck Surface | | | | | |
| Platelet/fibrin thrombus | None | Minimal, focal, or <25% of the surface | Mild, multi-focal or >25%-50% of the surface | Moderate, regional, diffuse 51-75% of the surface | Severe, diffuse; >75% of the surface |
| % Endothelialization | None | <25% of the surface | 25-50% of the surface | 51-75% of the surface | >75% of the surface |
| Neointima Formation | None | <25% of the area at the neck interface | 25-50% of the area at the neck interface | 51-75% of the area at the neck interface | >75% of the area at the neck interface |
| Sac | | | | | |
| Sac organization | None | >75% of the area with fibrin/platelet thrombus | 51-75% of the area with fibrin/platelet thrombus | 25-50% of the area with fibrin/platelet thrombus | <25% of the area with fibrin/platelet thrombus |
| Inflammation | None | ≤20 inflammatory cells/40xHPF | 21-100 inflammatory cells/40xHPF | 101-150 inflammatory cells/40xHPF | ≥150 inflammatory cells/40xHPF |
| Neo-angiogenesis | None | Focal, 1-3 vessels/40xHPF | >3 but ≤5 vessels/40xHPF | 6-10 vessels/40xHPF | ≥11 vessels/40xHPF |

Findings: Gross Evaluation

The findings of one animal from each of the "experimental" group (sample 1) and the "control" group (sample 2) are described below.

Gross evaluation of the aneurysm samples showed the embolic devices were clearly visible within the confines of the sac. The devices remained tightly compacted with no apparent perforations of the wall.

Radiographic evaluation showed filling of the aneurysm sacs with their respective devices. Slight protrusion of the "control" device beyond the level of the aneurysm neck was seen in sample 2. A summary of the semi-quantitative morphologic changes observed by light microscopy, using the scoring system shown in Table 1 above, is described in Table 2 below.

TABLE 2

| Specimen Number | Neck Surface | | | Sac | | |
|---|---|---|---|---|---|---|
| | Throm. | % Endo. | Neoint. | Org. | Inflam. | Neoang. |
| 1 ("experimental") | 0 | 4 | 4 | 4 | 4 | 3 |
| 2 ("control") | 0 | 4 | 4 | 3 | 1 | 1 |

Throm. = Platelet/fibrin thrombus;
% Endo. = % Endothelialization;
Neoint. = Neointima;
Inflam. = Inflammation;
Neoang. = Neoangiogenesis;
Org. = Organization Findings: Histologic Evaluation The parent and bifurcating lumen opposite the aneurysm were widely patent in both samples, and embolic masses were completely covered in both samples. Both samples also showed neck coverage with organized neointimal growth with partial to large area endothelial coverage.

Both aneurysm sacs showed occlusive filling with their respective devices, with organizing tissue matrix filling the spaces around the devices. Both samples showed a fill matrix composed mostly of loose collagen with interspersed spindle-shaped cells, chronic inflammatory cells, and mostly minimal to mild angiogenesis.

Sac inflammation was moderate to marked in samples 1. Inflammatory response was composed of chronic lympho-histiocytic and plasma cell infiltration of the sac matrix with macrophage and giant cell reactions to the "experimental" device thread surfaces. Sample 2 showed minimal inflammatory response to the devices. Without wishing to be bound by theory, the increased inflammatory response in the "experimental" sample may be important to facilitate remodeling into organized vascular tissue, rather than into disorganized scar tissue. Such scar tissue is typically seen with standard platinum coils, and may lead to recannulization.

Summary of Findings

At 30 days, gross evaluation showed the embolic devices tightly compacted within the confines of the sac with no apparent perforations of the wall. Histologically, the aneurysm samples showed mostly consistent degrees of inner sac organization with most samples showing overall moderate to marked organization composed of loosely arranged collagen and fibroblast matrix with minimal to mild angiogenesis. The neck surface of sample 1 showed moderate healing with mild to moderate endothelialization. Notably, sample 1 demonstrated superior organization and neoangeogenesis as compared to sample 2.

Figure 16A:
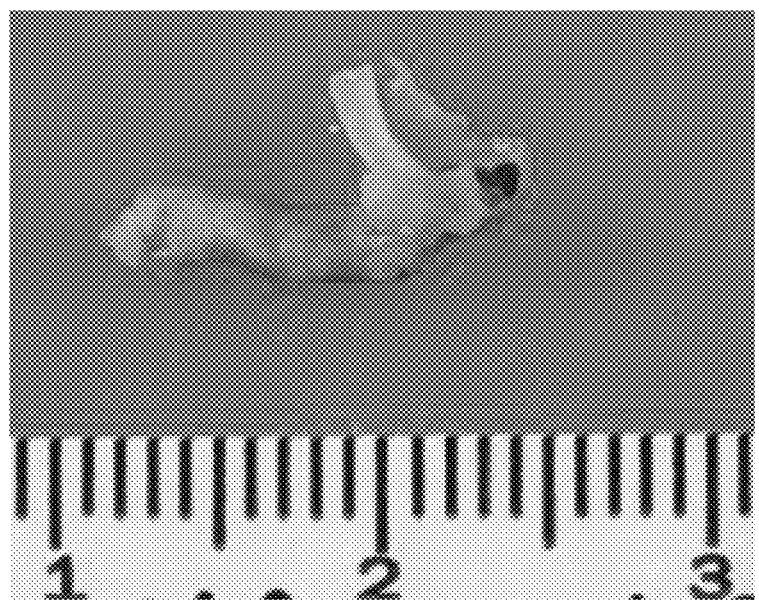
FIG. 16A illustrates a gross image of an embolized vessel from a longitudinal view in a rabbit model of an aneurysm embolized with an embolization device and method of deployment in accordance with the present disclosure after 30 days of healing.
Figure 16B:
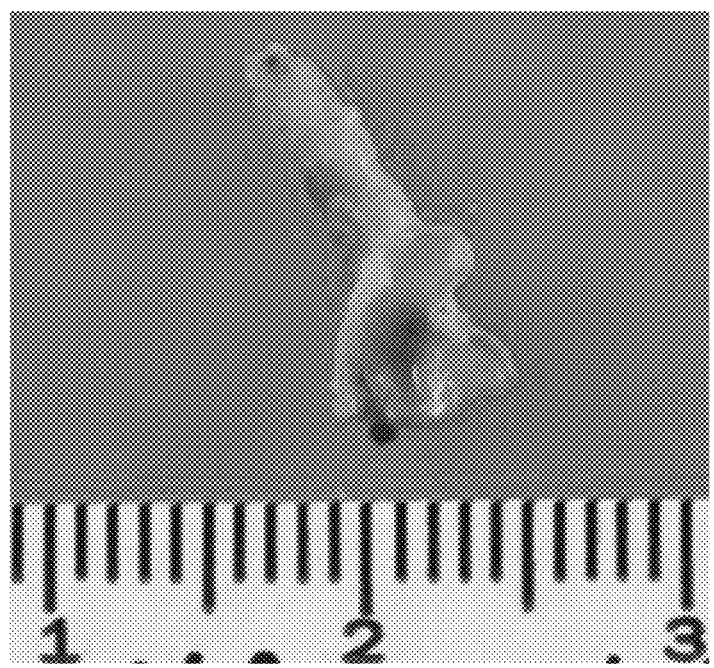
FIG. 16B illustrates a gross image of an embolized vessel from a luminal view in a rabbit model of an aneurysm embolized with an embolization device and method of deployment in accordance with the present disclosure after 30 days of healing.
Figure 16C:
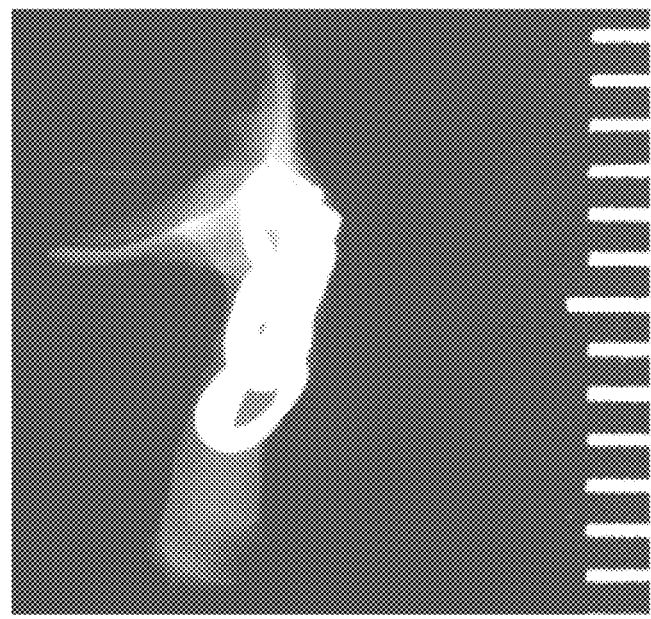
FIG. 16C illustrates a longitudinal radiograph view of the vessel shown in FIGS. 16A and 16B.

FIG. 16A, FIG. 16B, FIG. 16C, FIG. 17A, FIG. 17B, FIG. 17C, FIG. 17D, FIG. 17E, FIG. 17F, FIG. 18A, FIG. 18B, FIG. 18C, FIG. 18D, and FIG. 18E illustrate the gross, light microscopy, and histological assessments, respectively, of sample 1. FIG. 16A and FIG. 16B illustrate gross images of the embolized vessel from longitudinal and luminal views, respectively. FIG. 16C illustrates a longitudinal radiograph view of the same vessel.

Figure 17C:
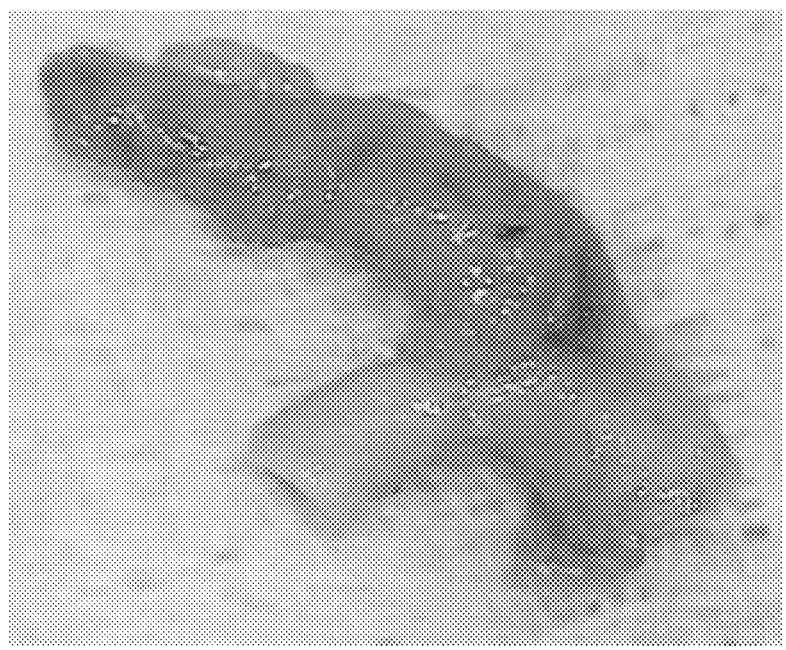
FIG. 17C illustrates the fully embolized vessel of FIG. 17B at a 16× magnification.
Figure 17D:
FIG. 17D illustrates the fully embolized vessel of FIG. 17B at a 40× magnification.
Figure 17E:
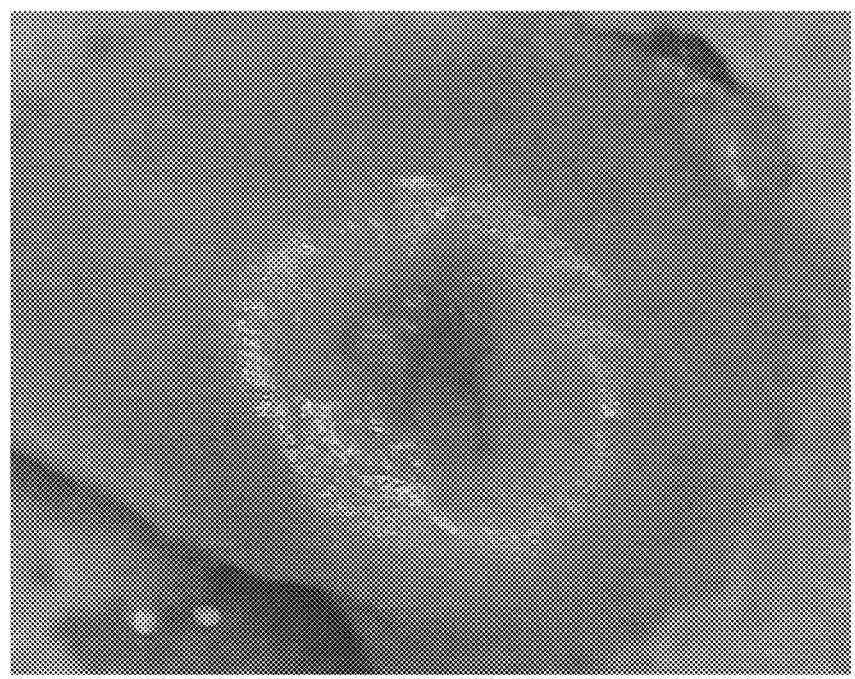
FIG. 17E illustrates a 40× magnification of the neck of the fully embolized vessel of FIG. 17B.
Figure 17F:

FIG. 17A illustrates an angiogram of the aneurysm at day 0, and FIG. 17B illustrates an angiogram of the same aneurysm 30 days after embolization. FIG. 17C illustrates the full embolized vessel after 30 days, at a 16× magnification, and FIG. 17D illustrates the same vessel at 40× magnification. FIG. 17E and FIG. 17F illustrate the neck of the embolized aneurysm after 30 days, at a 40× magnification.

FIG. 18A illustrates a whole mount coronal section through the sac (downward-facing arrow) and parent vessel (upward-facing arrow). FIG. 18B illustrates the aneurysm neck covered with neointimal growth and cross sections of the embolization device in accordance with the present disclosure underneath (arrows). FIG. 18C illustrates a close-up view of the neck with focally marked chronic inflammatory cell infiltration (arrow). FIG. 18D illustrates a large area of saccular matrix lymphocyte infiltration. FIG. 18E illustrates macrophage and giant cell reaction to the surface of the embolization device in accordance with the present disclosure (arrows). The samples in FIG. 18A and FIG. 18B were stained with MP stain; the samples in FIG. 18C, FIG. 18D, and FIG. 18E were stained with H&E stain.

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

The invention claimed is:

1. A method of deploying an embolization device, the method comprising:
   inserting into a vessel the embolization device, the embolization device comprising a fiber section comprising a plurality of polymeric electrospun fibers, wherein the embolization device further comprises a plurality of fiber sections, wherein each fiber section is separated by a linker; and
   applying an electrical current to one or more of the linkers, wherein the electrical current is from about 0.1 mA to about 100 mA.

2. The method of claim 1, wherein the linker comprises at least one electrolytically degradable material.

3. The method of claim 2, wherein the linker comprises a first metal having a first galvanic potential, and a second metal having a second galvanic potential different from the first galvanic potential.

4. The method of claim 1, wherein the linker comprises an electrically conductive polymer.

5. The method of claim 1, wherein the polymeric electrospun fibers comprise one or more polymers selected from the group consisting of non-resorbable polymers, resorbable polymers, natural polymers, or combinations thereof.

6. The method of claim 1, wherein the polymeric electrospun fibers comprise one or more polymers selected from the group consisting of polyethylene, polyethylene oxide, polyethylene terephthalate, polyester, polymethylmethacrylate, polyacrylonitrile, silicone, polyurethane, polycarbonate, polyether ketone ketone, polyether ether ketone, polyether imide, polyamide, polystyrene, polyether sulfone, polysulfone, polyvinyl acetate, polytetrafluoroethylene, polyvinylidene fluoride, polycaprolactone, polylactic acid, polyglycolic acid, polydioxanone, Poly(3-hydroxybutyrate-co-3-hydroxyvalerate), trimethylene carbonate, polydiols, polyesters, collagen, gelatin, fibrin, fibronectin, albumin, hyaluronic acid, elastin, chitosan, alginate, or combinations thereof.

7. The method of claim 1, further comprising a contrast agent selected from the group consisting of barium, tungsten, iodine, gadolinium, gold, platinum, tantalum, diatrizoate, metrizoate, ioxaglate, iopamidol, iohexol, ioxilan, iopromide, iodixanol, bismuth, bismuth (III) oxide, aid or combinations thereof.

8. The method of claim 7, wherein the contrast agent comprises about 1000 wt % tantalum.

9. The method of claim 1, wherein the fiber section excludes a core structure and comprises a twisted sheet of the polymeric electrospun fibers.

10. The method of claim 1, wherein the fiber section comprises from about 200 twists per meter to about 4000 twists per meter.

11. The method of claim 1, wherein the embolization device is at least partially formed into a shape selected from the group consisting of spherical, helical, conical, sinusoidal, J-shaped, S-shaped, shepherd's hook shaped, L-shaped, straight tail shaped, Omega-shaped, or combinations thereof.

12. The method of claim 1, wherein the embolization device comprises a coil, further comprising positioning the coil embolization device within a brain aneurysm to treat or reduce a risk of hemorrhagic stroke.

13. The method of claim 1, wherein the fiber sections and the linkers comprise different levels of radio-opacity.

14. The method of claim 1, wherein the fiber section has a volumetric characteristic configured to allow a packing density over 35%.

15. The method of claim 1, wherein the fiber section has a thickness within a range from about 15 μm to about 500 μm.

16. The method of claim 1, wherein the fiber section has a strain between about 25% to about 50% of an original length of the fiber section.

17. A method of deploying an embolization device, the method comprising:
    inserting into a vessel the embolization device, the embolization device comprising a fiber section comprising a plurality of polymeric electrospun fibers, wherein the embolization device further comprises a delivery vehicle, wherein the delivery vehicle is adhered to at least a portion of the fiber section by an adhesive; and
    applying electrothermal heat to one or more of the fiber portion and the delivery vehicle until at least a portion of the adhesive is melted.

18. The method of claim 17, wherein the adhesive comprises polyethylene terephthalate or polyurethane.

19. The method of claim 17, wherein the fiber section has a volumetric characteristic configured to allow a packing density over 35%.

20. The method of claim 17, wherein the fiber section has a thickness within a range from about 15 μm to about 500 μm.

21. The method of claim 17, wherein the fiber section has a strain between about 25% to about 50% of an original length of the fiber section.

22. The method of claim 17, wherein the fiber section excludes a core structure and comprises a twisted sheet of the polymeric electrospun fibers.

23. The method of claim 17, wherein the fiber section comprises from about 200 twists per meter to about 4000 twists per meter.

24. The method of claim 17, wherein the polymeric electrospun fibers comprise tantalum in a about of about 1000 wt % based on a weight of the polymeric electrospun fibers.

25. A method of deploying an embolization device, the method comprising:
    inserting into a vessel the embolization device, the embolization device comprising a fiber section comprising a plurality of polymeric electrospun fibers, wherein the embolization device further comprises a plurality of fiber sections, wherein each fiber section is separated by a linker; and
    applying electrothermal heat to one or more of the linkers.

26. The method of claim 25, wherein the embolization device comprises a coil, further comprising positioning the coil embolization device within a brain aneurysm to treat or reduce a risk of hemorrhagic stroke.

27. The method of claim 25, wherein the fiber sections and the linkers comprise different levels of radio-opacity.

28. The method of claim 25, wherein the fiber section has a volumetric characteristic configured to allow a packing density over 35%.

29. The method of claim 25, wherein the fiber section has a thickness within a range from about 15 μm to about 500 μm.

30. The method of claim 25, wherein the fiber section has a strain between about 25% to about 50% of an original length of the fiber section.

31. The method of claim 25, wherein the fiber section excludes a core structure and comprises a twisted sheet of the polymeric electrospun fibers.

32. The method of claim 25, wherein the fiber section comprises from about 200 twists per meter to about 4000 twists per meter.

33. The method of claim 25, wherein the polymeric electrospun fibers comprise tantalum in a about of about 1000 wt % based on a weight of the polymeric electrospun fibers.

34. The method of claim 17, wherein the embolization device comprises a coil, further comprising positioning the coil embolization device within a brain aneurysm to treat or reduce a risk of hemorrhagic stroke.

* * * * *